United States Patent
An et al.

(10) Patent No.: US 10,426,962 B2
(45) Date of Patent: Oct. 1, 2019

(54) LEADLESS PACEMAKER USING PRESSURE MEASUREMENTS FOR PACING CAPTURE VERIFICATION

(71) Applicant: CARDIAC PACEMAKERS, INC., St. Paul, MN (US)

(72) Inventors: Qi An, Blaine, MN (US); Jeffrey E. Stahmann, Ramsey, MN (US); Pramodsingh Hirasingh Thakur, Woodbury, MN (US); Yinghong Yu, Shoreview, MN (US); Michael J. Kane, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 42 days.

(21) Appl. No.: 15/635,921

(22) Filed: Jun. 28, 2017

(65) Prior Publication Data
US 2018/0008831 A1 Jan. 11, 2018

Related U.S. Application Data

(60) Provisional application No. 62/359,358, filed on Jul. 7, 2016.

(51) Int. Cl.
*A61N 1/00* (2006.01)
*A61N 1/37* (2006.01)
(Continued)

(52) U.S. Cl.
CPC ......... *A61N 1/371* (2013.01); *A61N 1/36564* (2013.01); *A61N 1/3704* (2013.01); *A61N 1/3756* (2013.01); *A61N 1/37288* (2013.01)

(58) Field of Classification Search
CPC .. A61N 1/371; A61N 1/36564; A61N 1/3756; A61N 1/3704; A61N 1/37288
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — Scott M. Getzow
(74) *Attorney, Agent, or Firm* — Seager, Tufte & Wickhem LLP

(57) ABSTRACT

Methods, devices, and systems for performing pacing capture verification in implantable medical devices such as a leadless cardiac pacemakers using a pressure signal. An example medical device includes a pressure sensor and is configured to monitor for an evoked capture response using the pressure sensor following pace delivery. Various factors of the pressure waveform may be used including the use of threshold, templating, and slope, as well as comparing cross-domain sensed events including using a fiducial point from the pressure signal for comparison to an acoustic, electrical, or motion event, or the use of data obtained from a second device which may be implanted, wearable, or external to the patient.

20 Claims, 14 Drawing Sheets

(51) Int. Cl.
*A61N 1/372* (2006.01)
*A61N 1/375* (2006.01)
*A61N 1/365* (2006.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,702,427 A | 12/1997 | Ecker et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |

(56) References Cited

U.S. PATENT DOCUMENTS

| | | |
|---|---|---|
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,505,077 B1 | 1/2003 | Kast et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,575 B2 | 12/2006 | Ostroff et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,189,204 B2 | 3/2007 | Ni et al. |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |

(56) References Cited

U.S. PATENT DOCUMENTS

| | | |
|---|---|---|
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,376,458 B2 | 5/2008 | Palreddy et al. |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,477,935 B2 | 1/2009 | Palreddy et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,340 B2 | 8/2010 | Sanghera et al. |
| 7,783,362 B2 | 8/2010 | Whitehurst et al. |
| 7,792,588 B2 | 9/2010 | Harding |
| 7,797,059 B1 | 9/2010 | Bomzin et al. |
| 7,801,596 B2 | 9/2010 | Fischell et al. |
| 7,809,438 B2 | 10/2010 | Echt et al. |
| 7,809,441 B2 | 10/2010 | Kane et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |

(56) References Cited

U.S. PATENT DOCUMENTS

| | | |
|---|---|---|
| 8,036,743 B2 | 10/2011 | Savage et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,079,959 B2 | 12/2011 | Sanghera et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,116,867 B2 | 2/2012 | Ostroff |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,157,813 B2 | 4/2012 | Ko et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,195,308 B2 | 6/2012 | Frank et al. |
| 8,200,341 B2 | 6/2012 | Sanghera et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,034 B2 | 12/2012 | Patangay et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,399 B2 | 7/2013 | Degroot et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,483,843 B2 | 7/2013 | Sanghera et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,878 B2 | 10/2013 | Allavatam et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,626,310 B2 | 1/2014 | Barror et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |

(56) References Cited

U.S. PATENT DOCUMENTS

| | | |
|---|---|---|
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,325 B2 | 11/2014 | Boling et al. |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,072,914 B2 | 7/2015 | Greenhut et al. |
| 9,079,035 B2 | 7/2015 | Sanghera et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishier et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |

(56) References Cited

U.S. PATENT DOCUMENTS

| | | |
|---|---|---|
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0247707 A1* | 11/2006 | Meyer ............... A61B 5/04525 607/28 |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1* | 4/2007 | Jacobson ............. A61N 1/3708 607/4 |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0275522 A1 | 11/2008 | Dong et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0264949 A1 | 10/2009 | Dong et al. |
| 2009/0266573 A1 | 10/2009 | Engmark et al. |
| 2009/0270937 A1 | 10/2009 | Yonce et al. |
| 2009/0275843 A1* | 11/2009 | Karamanoglu .... A61B 5/02028 600/486 |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0106213 A1* | 4/2010 | Hilpisch ............... A61N 1/371 607/23 |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |

(56) References Cited

U.S. PATENT DOCUMENTS

| | | |
|---|---|---|
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0305646 A1 | 12/2010 | Schulte et al. |
| 2010/0312309 A1 | 12/2010 | Harding |
| 2010/0331905 A1 | 12/2010 | Li et al. |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0125208 A1 | 5/2011 | Karst et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0178567 A1 | 7/2011 | Pei et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0029335 A1 | 2/2012 | Sudam et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0030484 A1 | 1/2013 | Zhang et al. |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0245709 A1 | 9/2013 | Bohn et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0310890 A1 | 11/2013 | Sweeney |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |

(56) References Cited

U.S. PATENT DOCUMENTS

| | | |
|---|---|---|
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0163631 A1 | 6/2014 | Maskara et al. |
| 2014/0169162 A1 | 6/2014 | Romano et al. |
| 2014/0172060 A1 | 6/2014 | Bomzin et al. |
| 2014/0180306 A1 | 6/2014 | Grubac et al. |
| 2014/0180366 A1 | 6/2014 | Edlund |
| 2014/0207013 A1 | 7/2014 | Lian et al. |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222099 A1 | 8/2014 | Sweeney |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236253 A1 | 8/2014 | Ghosh et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0032173 A1 | 1/2015 | Ghosh |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0142069 A1 | 5/2015 | Sambelashvili |
| 2015/0142070 A1 | 5/2015 | Sambelashvili |
| 2015/0157861 A1 | 6/2015 | Aghassian |
| 2015/0165199 A1 | 6/2015 | Karst et al. |
| 2015/0173655 A1 | 6/2015 | Demmer et al. |
| 2015/0182751 A1 | 7/2015 | Ghosh et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297902 A1 | 10/2015 | Stahmann et al. |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0360036 A1 | 12/2015 | Kane et al. |
| 2016/0007873 A1 | 1/2016 | Huelskamp et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0045131 A1 | 2/2016 | Siejko |
| 2016/0045132 A1 | 2/2016 | Siejko |
| 2016/0045136 A1 | 2/2016 | Siejko et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0144190 A1 | 5/2016 | Cao et al. |
| 2016/0151621 A1 | 6/2016 | Maile et al. |
| 2016/0175601 A1 | 6/2016 | Nabutovsky et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0271406 A1 | 9/2016 | Maile et al. |
| 2016/0277097 A1 | 9/2016 | Ludwig et al. |
| 2016/0296131 A1 | 10/2016 | An et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0021159 A1 | 1/2017 | Reddy et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056665 A1 | 3/2017 | Kane et al. |
| 2017/0056666 A1 | 3/2017 | Kane et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatam et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368360 A1 | 12/2017 | Hahn et al. |
| 2018/0008829 A1 | 1/2018 | An et al. |
| 2018/0008831 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0021584 A1 | 1/2018 | An et al. |
| 2018/0036527 A1 | 2/2018 | Reddy et al. |
| 2018/0056075 A1 | 3/2018 | Hahn et al. |
| 2018/0056079 A1 | 3/2018 | Hahn et al. |
| 2018/0078773 A1 | 3/2018 | Thakur et al. |
| 2018/0116593 A1 | 5/2018 | An et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |

(56) References Cited

FOREIGN PATENT DOCUMENTS

| | | |
|---|---|---|
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9407567 A | 4/1994 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |
| WO | 2016022397 A1 | 2/2016 |
| WO | 2016118735 A1 | 7/2016 |

OTHER PUBLICATIONS

International Search Report and Written Opinion dated Sep. 6, 2017 for International Application No. PCT/US2017/039726.
"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Notification of Transmittal of the International Search Report and the Written Opinion of the International Searching Authority, or the Declaration, dated Jan. 29, 2016, 15 pages.
Notification of Transmittal of the International Search Report and the Written Opinion of the International Searching Authority, or the Declaration, dated Mar. 9, 2016, 10 pages.
Seyedi et al., "A Survey on Intrabody Communications for Body Area Network Application," IEEE Transactions on Biomedical Engineering, vol. 60(8): 2067-2079, 2013.
Spickler et al., "Totally Self-Contained Intracardiac Pacemaker," Journal of Electrocardiology, vol. 3(3&4): 324-331, 1970.
Wegmüller, "Intra-Body Communication for Biomedical Sensor Networks," Diss. ETH, No. 17323, 1-173, 2007.

\* cited by examiner

LEADLESS PACEMAKER USING PRESSURE MEASUREMENTS FOR PACING CAPTURE VERIFICATION

CROSS REFERENCE TO RELATED APPLICATIONS

The present application claims the benefit of and priority to U.S. Provisional Patent Application Ser. No. 62/359,358, filed Jul. 7, 2016, the disclosure of which is incorporated herein by reference.

BACKGROUND

Some implantable medical devices such as pacemakers can be used to treat patients suffering from various heart conditions that can result in a reduced ability of the heart to deliver sufficient amounts of blood to a patient's body. In some cases, heart conditions may lead to rapid, irregular, and/or inefficient heart contractions. To help alleviate some of these conditions, various devices (e.g., pacemakers, defibrillators, etc.) can be implanted in a patient's body. Such devices are often used to monitor heart activity and provide electrical stimulation to the heart to help the heart operate in a more normal, efficient and/or safe manner.

Prior pacemakers have generally used one or more transvenous leads with intracardiac electrodes to deliver pacing therapy. Newer generation devices may take the form of a leadless cardiac pacemaker (LCP), such as the Medtronic Micra™ or Nanostim™ leadless pacemakers, as well as other LCP products that are in development.

The pacing pulse delivered by a pacemaker is intended to evoke a response by the myocardium. When the pacing pulse causes the desired evoked response (typically an effective and appropriately times contraction of one or more chambers), the pacing pulse is said to have "captured" the relevant chamber. For purposes herein, the evoked response to a pace pulse that captures the relevant chamber is termed an "evoked capture response." Typically effective capture requires at least a threshold voltage or current be output; this capture threshold can vary in a given patient for various reasons. Setting the output energy of a pacemaker too low can fail to ensure reliable capture; setting the output energy too high can waste current and reduce battery life of the typically non-rechargeable battery. As a result, periodic or occasional confirmation and/or adjustment of the output energy of a pacemaker may be performed to ensure reliable capture without wasting energy. Such adjustment requires the ability to verify pacing capture. Some devices may be setup to verify pacing capture on an ongoing bases, rather than as a part of a test procedure. New and alternative methods for pacing capture verification are desired.

OVERVIEW

In selected embodiments, the present invention comprises methods, devices, and/or systems for performing pacing capture verification in implantable medical devices, such as leadless cardiac pacemakers, using a pressure signal. An example implantable medical device includes a pressure sensor and is configured to monitor for an evoked capture response using the pressure sensor following pace delivery. Various factors of the pressure waveform may be used including the use of threshold, templating, and slope, as well as comparing cross-domain sensed events including using a fiducial point from the pressure signal for comparison to an acoustic, electrical, or motion event, or the use of data obtained from a second device which may be implanted, wearable, or external to the patient.

A first non-limiting example comprising an implantable medical device comprising at least first and second electrodes for at least one of delivering therapy or sensing electrical signals; a pressure sensor for sensing intracardiac pressure; and operational circuitry coupled to the electrodes and the pressure sensor; wherein the operational circuitry is configured to perform a pressure based capture verification process including the following: deliver an electrical pacing stimulus to the heart of a patient using the at least first and second electrodes; monitor for an evoked capture response indicating the electrical pacing stimulus was captured using the pressure sensor; and if the evoked capture response is detected, conclude that the electrical pacing stimulus captured at least a portion of the patient's heart; and if the evoked capture response is not detected, conclude that the electrical pacing stimulus did not capture the patient's heart.

A second non-limiting example takes the form of a medical device as in the first non-limiting example, wherein the operational circuitry is configured to monitor for an evoked capture response by obtaining a signal received with the pressure sensor over a period of time following delivery of the electrical pacing stimulus, extracting a feature from the pressure signal, and comparing the extracted feature to a feature threshold, such that: if the feature threshold is exceeded, the operational circuitry is configured to conclude that the evoked capture response has been detected; and if the feature threshold is not exceeded, the operational circuitry is configured to conclude that the evoked capture response has not been detected.

A third non-limiting example takes the form of a medical device as in the second non-limiting example, wherein the extracted feature is a peak pressure during systole and the feature threshold is a pressure threshold. A fourth non-limiting example takes the form of a medical device as in the second non-limiting example, wherein the extracted feature is a minimum pressure during diastole, and the feature threshold is a minimum pressure threshold for diastole. A fifth non-limiting example takes the form of a medical device as in the second non-limiting example, wherein the extracted feature is a peak rate of change of pressure during systole, and the feature threshold is a minimum rate of change of pressure. A sixth non-limiting example takes the form of a medical device as in the second non-limiting example, wherein the extracted feature is a minimum rate of change of pressure, and the feature threshold is a minimum rate of change of pressure. A seventh non-limiting example takes the form of a medical device as in the second non-limiting example, wherein the extracted feature is an area under the curve of a measured pressure over a period of time, and the feature threshold is a minimum area.

An eighth non-limiting example takes the form of a medical device as in any of the second to seventh examples, wherein the operational circuitry is configured to perform an evoked pressure signal initialization process in which: the operational circuitry issues one or more electrical pacing stimulus to the heart of the patient using the at least first and second electrodes, the one or more electrical pacing stimulus being delivered using pacing parameters that are expected to capture the heart; the operational circuitry obtains signals from the pressure sensor and determines an expected feature value using obtained pressure signals corresponding to evoked capture responses; the operational circuitry sets the feature threshold in relation to the expected feature value.

A ninth non-limiting example takes the form of a medical device as in any of the second to seventh non-limiting examples, wherein the operational circuitry is configured to perform an evoked pressure signal initialization process in which: the medical device communicates with a second device, the second device being configured to determine whether pacing pulses delivered by the medical device capture the heart; the operational circuitry issues at least one electrical pacing stimulus to the heart of the patient using the at least first and second electrodes and receives confirmation from the second device that capture has occurred generating one or more confirmed evoked capture responses; the operational circuitry obtains signals from the pressure sensor and determines an expected feature value corresponding to the one or more confirmed evoked capture responses; the operational circuitry sets the feature threshold in relation to the expected feature value.

A tenth non-limiting example takes the form of a medical device as in any of the second to seventh non-limiting examples, wherein the operational circuitry is configured to perform an evoked pressure signal initialization process in which: the operational circuitry issues at least one electrical pacing stimulus to the heart of the patient using the at least first and second electrodes; the operational circuitry analyzes an electrical signal sensed from the heart and determines that capture has occurred generating one or more confirmed evoked capture responses; the operational circuitry obtains signals from the pressure sensor and determines an expected feature value corresponding to the one or more confirmed evoked capture responses; the operational circuitry sets the feature threshold in relation to the expected feature value.

An eleventh non-limiting example takes the form of a medical device as in the first non-limiting example, wherein the operational circuitry is configured to monitor for an evoked capture response by obtaining a signal received with the pressure sensor over a period of time following delivery of the electrical pacing stimulus, and comparing the obtained pressure signal to an evoked pressure signal template, such that: if the evoked pressure signal template matches the obtained pressure signal, the operational circuitry is configured to conclude that the evoked capture response has been detected; and if the evoked pressure signal template fails to match the obtained pressure signal, the operational circuitry is configured to conclude that the evoked capture response has not been detected.

A twelfth non-limiting example takes the form of a medical device as in the eleventh non-limiting example, wherein the operational circuitry is configured to perform an evoked pressure signal initialization process in which: the operational circuitry issues one or more electrical pacing stimulus to the heart of the patient using the at least first and second electrodes, the one or more electrical pacing stimulus being delivered at an energy that is expected to capture the heart; the operational circuitry obtains signals from the pressure sensor and determines an evoked pressure signal template.

A thirteenth non-limiting example takes the form of a medical device as in the eleventh non-limiting example, wherein the operational circuitry is configured to perform an evoked pressure signal initialization process in which: the medical device communicates with a second device, the second device being configured to determine whether pacing pulses delivered by the medical device capture the heart; the operational circuitry issues at least one electrical pacing stimulus to the heart of the patient using the at least first and second electrodes and receives confirmation from the second device that capture has occurred generating one or more confirmed evoked capture responses; the operational circuitry obtains signals from the pressure sensor corresponding to the confirmed evoked capture responses, and determines an evoked pressure signal template A fourteenth non-limiting example takes the form of a medical device as in the eleventh non-limiting example, wherein the operational circuitry is configured to perform an evoked pressure signal initialization process in which: the operational circuitry issues at least one electrical pacing stimulus to the heart of the patient using the at least first and second electrodes; the operational circuitry analyzes an electrical signal sensed from the heart and determines that capture has occurred generating one or more confirmed evoked capture responses; the operational circuitry obtains signals from the pressure sensor corresponding to the confirmed evoked capture responses, and determines an evoked pressure signal template.

A fifteenth non-limiting example takes the form of a medical device as in any of the eleventh to fourteenth non-limiting examples, further comprising a posture sensor, wherein the operational circuitry is configured to store a plurality of template evoked pressure signal templates corresponding to at least first and second postures of the patient.

A sixteenth non-limiting example takes the form of a medical device as in any of the eleventh to fourteenth non-limiting examples, wherein the first medical device is configured for implantation in a first chamber of the heart, and the second medical device is configured for implantation in a second chamber of the heart, wherein at least one of the first and second medical devices is configured to store a plurality of evoked pressure signal templates including: an evoked pressure signal template for capture by only one of the first and second medical devices; and an evoked pressure signal template corresponding to capture by both of the first and second medical devices.

A sixteenth non-limiting example takes the form of a medical device as in the first non-limiting example, wherein the operational circuitry is configured to monitor for an evoked capture response by obtaining a signal received with the pressure sensor over a period of time following delivery of the electrical pacing stimulus, and is further configured to: identify a first point in time at which a peak pressure signal occurs; identify a second point in time at which a selected cardiac event takes place using a heart sound detectable within the pressure signal, the heart sound relating to an atrial event, wherein the electrical pacing stimulus is configured to excite a ventricle; calculate an interval between the first and second points in time; and determine whether an evoked capture response has been detected using the interval; wherein: if the interval is shorter than a threshold, the operational circuitry is configured to conclude that the evoked capture response has occurred; and if the interval is longer than a threshold, the operational circuitry is configured to conclude that the evoked capture response has not occurred.

A seventeenth non-limiting example takes the form of a medical device as in the first non-limiting example, wherein the operational circuitry is configured to monitor for an evoked capture response by: obtaining a pressure signal received with the pressure sensor over a period of time following delivery of the electrical pacing stimulus and a cardiac electrical signal; determining an R-wave time at which the electrical R-wave signal of the heart occurs following the electrical pacing stimulus; determining a pressure time at which predefined event in the obtained pressure signal occurs; calculating an interval between the R-wave time and the pressure time; comparing the interval to a threshold and: if the interval exceeds the threshold, determining that the evoked capture response has occurred; and if the interval does not exceed the threshold, determining that the evoked capture response has not occurred.

An eighteenth non-limiting example takes the form of a medical device as in the first non-limiting example, further comprising a motion sensor, wherein the operational circuitry is configured to monitor for an evoked capture response by: obtaining a pressure signal received with the pressure sensor over a period of time following delivery of the electrical pacing stimulus and a motion signal sensed with the motion sensor; determining a motion time at which the motion sensor detects cardiac movement following the electrical pacing stimulus; determining a pressure time at which a peak or minimum pressure in the obtained signal occurs; determining whether each of: (a) the pressure signal exceeds a pressure threshold; and (b) the motion time and the pressure time temporally correlate to one another; if both a) and b) occur, determining that the evoked capture response has occurred; and if one or both of a) and b) do not occur, determining that the evoked capture response has not occurred.

A nineteenth non-limiting example takes the form of a medical device as in the first non-limiting example, wherein the operational circuitry is configured to monitor for an evoked capture response by: obtaining a pressure signal received with the pressure sensor over a period of time following delivery of the electrical pacing stimulus; determining a maximum slope of the pressure signal; and if the maximum slope is greater than a threshold, determining that the evoked capture response has not occurred; or if the maximum slope is not greater than the threshold, determining that the evoked capture response has occurred.

A twentieth non-limiting example takes the form of a medical device as in any of the first to nineteenth non-limiting examples, wherein the operational circuitry is configured to perform an electrical pacing capture verification process in addition to the pressure based capture verification process, the electrical pacing capture verification process comprising one or more of: electrically comparing a sensed electrical signal after delivery of therapy to one or more thresholds; or electrically comparing a sensed electrical signal after delivery of therapy to a template; wherein the operational circuitry is configured to use the electrical pacing capture verification process as a default capture verification process, and to reference the pressure-based capture verification process in the event that at least one of: the electrical pacing capture verification process becomes unavailable or unreliable; or the electrical pacing capture verification process returns one or more ambiguous results.

A twenty-first non-limiting example takes the form of a medical device as in any of the first to twentieth non-limiting examples, wherein the medical device takes the form of a leadless cardiac pacemaker configured for implantation and operation within the left ventricle of a patient.

A twenty-second non-limiting example takes the form of a medical device as in any of the first to twentieth non-limiting examples, wherein the medical device takes the form of a leadless cardiac pacemaker configured for implantation and operation within the right ventricle of a patient.

A twenty-third non-limiting example takes the form of a medical device as in any of the first to twentieth non-limiting examples, wherein the medical device takes the form of a leadless cardiac pacemaker configured for implantation and operation within at least one of the left or right atria of a patient.

A twenty-fourth non-limiting example takes the form of a medical device as in any of the first to twenty-third non-limiting examples, in which the operational circuitry is configured, in response to a finding that an evoked capture response is not detected, to determine whether a change in atrio-ventricular delay is likely a cause of a failure to capture the heart leading to a lack of evoked capture response.

A twenty-fifth non-limiting example takes the form of a medical device as in the twenty-fourth non-limiting example, wherein the operational circuitry is configured to communicate with a second implantable device to facilitate determination of whether a change in atrio-ventricular delay is likely a cause of a failure to capture the heart.

A twenty-sixth non-limiting example takes the form of a medical device as in any of the first to twenty-fifth non-limiting examples, in which the operational circuitry is configured, in response to a finding that an evoked capture response is not detected, to determine whether an intrinsic R-wave has taken place prior to the pacing therapy.

A twenty-seventh non-limiting example takes the form of a medical device as in any of first to twenty-sixth non-limiting examples further comprising a chemical sensor for monitoring for the presence or quantity of a selected chemical in the patient; and the operational circuitry is configured to perform an evoked pressure signal initialization process in response to a change in an output of the chemical sensor.

A twenty-eighth non-limiting example takes the form of a medical device as in any of first to twenty-seventh non-limiting examples wherein the medical device is configured to detect respiration of a patient; and the operational circuitry is configured to perform an evoked pressure signal initialization process in response to a change in the patient's respiration.

A twenty-ninth non-limiting example takes the form of a medical device as in any of first to twenty-eighth non-limiting examples, wherein the medical device is configured to detect sleep state of a patient; and the operational circuitry is configured to perform an evoked pressure signal initialization process in response to a change in the patient's sleep state.

A thirtieth non-limiting example takes the form of a medical device as in any of first to twenty-ninth non-limiting examples, wherein: the medical device is configured to detect an activity level of a patient; and the operational circuitry is configured to perform an evoked pressure signal initialization process in response to a change in the patient's activity level.

A thirty-first non-limiting example takes the form of a medical device as in any of the first to thirtieth non-limiting examples, wherein the operational circuitry is configured to perform an evoked pressure signal initialization process in response to a change in pacing parameters.

A thirty-second non-limiting example takes the form of a medical device as in any of the first to thirty-first non-limiting examples, wherein: the medical device is configured to detect arrhythmias of the patient's heart; and the operational circuitry is configured to perform the evoked pressure signal initialization process in response to detecting an arrhythmia.

A thirty-third non-limiting example takes the form of a method of treating a patient comprising implanting a medical device as in any of the first to thirty-second non-limiting examples, and activating the device to deliver pacing therapy and perform pacing capture verification.

A thirty-fourth non-limiting example takes the form of a method of verifying pacing capture comprising using a device as in any of the first to thirty-second non-limiting examples to perform pacing capture verification using pressure signals.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
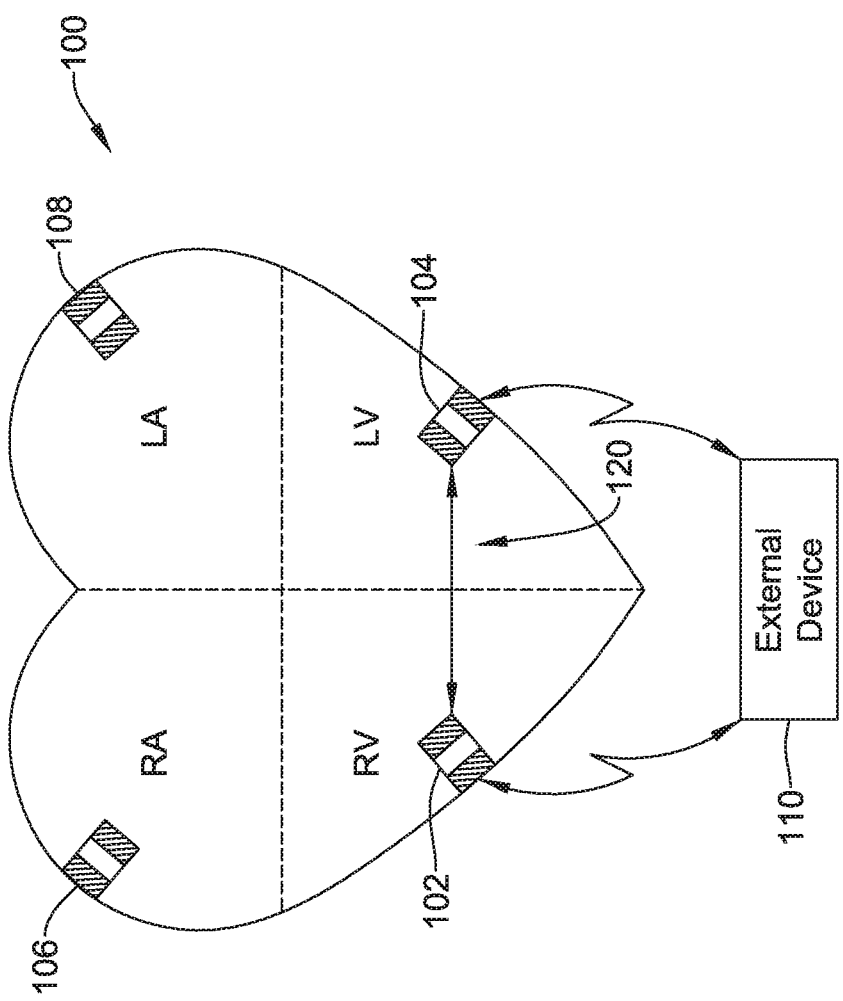
FIG. 1 illustrates implantation of one or more medical devices in the heart of a patient.

FIG. 1 illustrates implantation of one or more medical devices in the heart of a patient. The patient's heart 100 is shown in isolation for illustrative purposes. The medical devices may take the form of pacemakers. For example, a first leadless cardiac pacemaker (LCP) is shown implanted in the right ventricle (RV), at 102, and a second LCP is shown implanted in the left ventricle (LV), at 104. The use of two LCP devices in one patient is optional; if desired only the RV LCP 102 may be provided, or, instead, only the LV LCP 104 may be provided. Other positions may be used, including, for example, providing an LCP in the right atrium (RA) or left atrium (LA), as shown at 106, 108, respectively.

In other examples, an additional implantable device such as a subcutaneous defibrillator (not shown) may be included. Subcutaneous implantable defibrillators may include, for example, the Emblem S-ICD System™ offered by Boston Scientific Corporation. Combinations of subcutaneous defibrillators and LCP devices are discussed, for example, in US PG Patent Publication Nos. 20160059025, 20160059024, 20160059022, 20160059007, 20160038742, 20150297902, 20150196769, 20150196758, 20150196757, and 20150196756, the disclosures of which are incorporated herein by reference. The subcutaneous defibrillator and LCP may, for example, exchange data related to cardiac function or device status, and may operate together as a system to ensure appropriate determination of cardiac condition (such as whether or not a ventricular tachyarrhythmia is occurring), as well as to coordinate therapy such as by having the LCP deliver antitachycardia pacing in an attempt to convert certain arrhythmias before the subcutaneous defibrillator delivers a defibrillation shock. A sub sternal defibrillator may be used instead of the subcutaneous defibrillator, as described, for example, in US PG Patent Pub. No. 2017/0021159, titled SUB STERNAL PLACEMENT OF A PACING AND/OR DEFIBRILLATING ELECTRODE.

Communication may take place, as illustrated at 120, between the LCP devices 102 and 104, for example. Any two or more of devices 102, 104, 106, 108 may communicate with one another. In addition, any of the implanted devices 102, 104, 106, 108 may communicate with an external device such as a programmer. Such communication may use a conducted communication signal—where a voltage or current output is generated at the electrodes of the device and sensed at a second device, or may use inductive telemetry or RF telemetry, such as Medradio, ISM, or Bluetooth communication, for example, in which a radiated signal is generated by an antenna or coil; any other form of communication may be used as well, including acoustic or optical communication. Communications may serve the purpose of coordinating or commanding therapy between devices, sharing information such as device diagnostics or indications of the patient's medical status, for example, the cardiac rhythm of the patient or other cardiac condition, or to program one or more of the implanted devices, or any other purpose.

Figure 2:
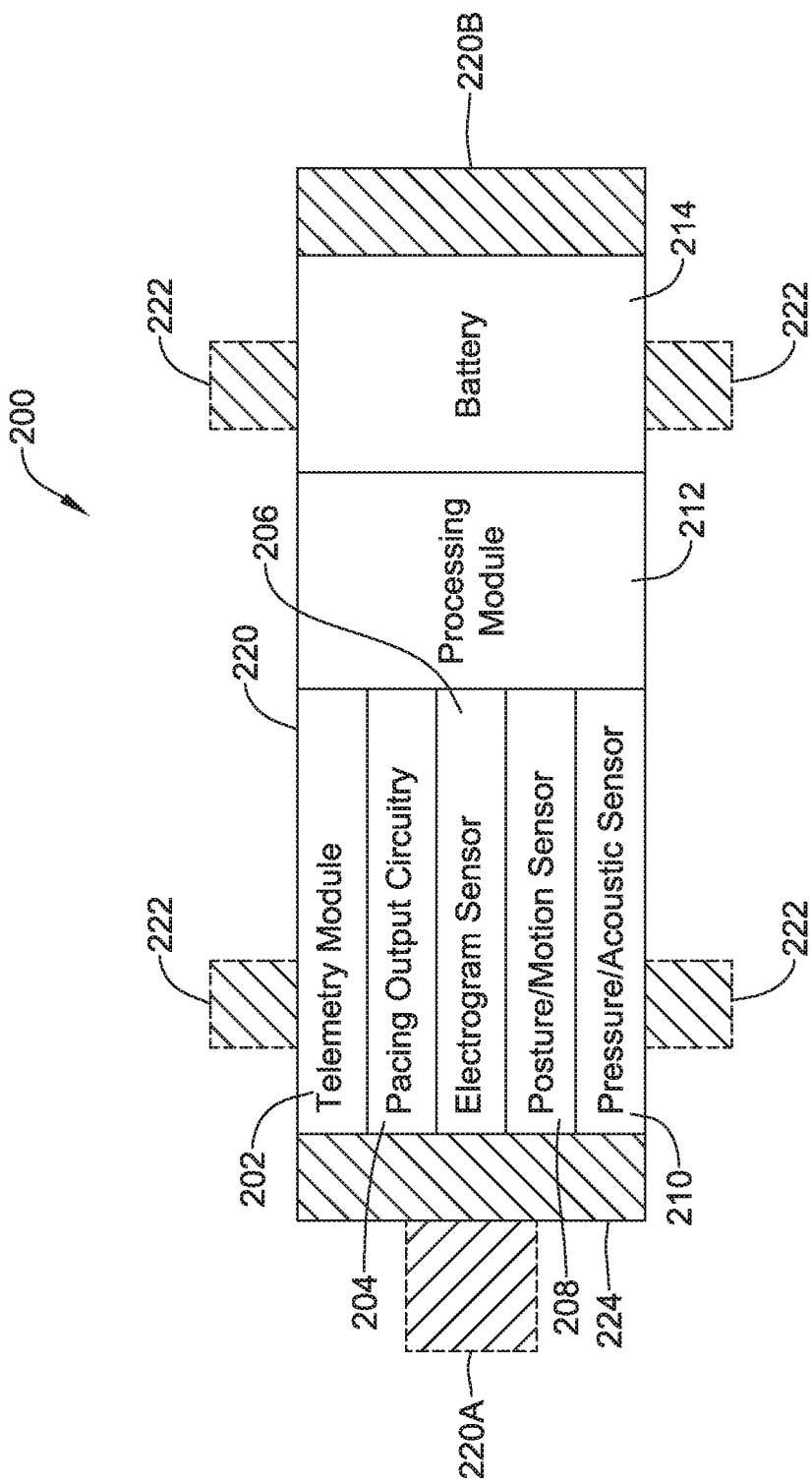
FIG. 2 shows an illustrative implantable medical device.

FIG. 2 is an illustration of an exemplary leadless cardiac pacemaker (LCP) 200. As can be seen in FIG. 2, LCP 200 may be a compact device with all components housed within LCP 200 or directly on housing 230. For example, LCP 200 may include operational circuitry including a telemetry module 202, pacing output circuitry 204, and sensing modules including, for example, an electrogram sensor 206, a posture or motion sensor 208, and a pressure or acoustic sensor 210.

The operational circuitry may include a processing module, as indicated at 212. The processing module 212 may include, for example and without limitation, a state machine, a microcontroller, or a microprocessor, and/or various logic circuitry including as needed dedicated signal processing circuitry. The implantable device is powered by battery 214. The battery 214 may use any suitable battery chemistry and may be either non-rechargeable or rechargeable (if battery 214 is rechargeable, there would also be a recharging circuit and coil or transducer for recharging the battery 214). Battery 214 may instead take the form of a capacitor or super-capacitor for rechargeable or on-demand externally powered use.

The illustrative device 200 further includes electrodes shown at 220A, 220B for use in receiving electrical signals and/or outputting electrical therapy or signals. Optional alternative positions for electrodes are also shown at 222. An anchoring device may be provided as indicated at 224 and may include, for example, tines, a helical coil, or other anchoring apparatus.

The telemetry module may include an antenna or inductive element and associated frequency generating and control circuitry for use as an RF telemetry or inductive telemetry module using, for example, the ISM, Bluetooth, or Medradio bands, as desired, or using an inductive telemetry solution, if desired. In some examples, the telemetry module 202 may be adapted to provide output communication signals via conducted communication by simply outputting electrical energy via the electrodes 220A, 220B and/or 222.

The electrogram sensor may include, for example, amplifiers and filtering circuitry coupled to at least first and second electrodes (such as those at 220A, 220B, and/or 222) for receiving input electrical signals including the cardiac electrogram. As used herein, the electrogram is the cardiac signal as received within or very near to cardiac tissue, as opposed to the far-field electrocardiogram, which generally refers to the cardiac electrical signal as observed from a greater distance such as from outside of the patient or outside of the ribcage. Typically the electrogram will be converted from analog to digital form for analysis by the processing module 212, though this is not required.

The posture/motion sensor may take the form of one or more accelerometers, for example, a multi-axis accelerometer including first, second and third transducers. The use of accelerometers to monitor posture and/or cardiac motion is known in the art. Some discussion may be found in US PG Patent Pub. Nos. 2017/0056665 and 2017/0056666, the disclosures of which are incorporated herein by reference.

The pressure or acoustic sensor 210 may comprises a pressure transducer. Depending on the frequency selected for analysis, heart sounds (such as S1, S2, S3, and/or S4, which have relatively higher frequency) or changes in blood pressure (lower frequency) may be monitored by the pressure or acoustic sensor. The output of the pressure or acoustic sensor may, for example, be analyzed in two separate channels to allow parallel processing of pressure signals and heart sound signals, if desired. Alternatively or additionally, the output of the pressure or acoustic sensor may also be analyzed for respiratory sounds or cardiac murmurs which have energy at higher frequencies than S1-S4 heart sounds, and may be analyzed via their own processing channel.

The processing module 212 is coupled to each of these elements 202, 204, 206, 208, 210, and together these make up the operational circuitry of the device 200. Additional elements may be provided including, for example, blood-oxygen sensors, and other sensors which measure physiological parameters of the patient. Although described with respect to FIG. 2 as separate sensing modules, in some examples, several of elements 202, 204, 206, 208, 210, 212 may be implemented on a single integrated circuit chip. In other examples, the illustrated components may be implemented in multiple integrated circuit chips that are in electrical communication with one another.

The modules 202, 204, 206, 208, 210, 212 and battery 214 may be enclosed and hermetically sealed within housing 230. Housing 230 may generally include any material that is known as safe for implantation within a human body to prevent ingress of from fluids and/or tissue when LCP 200 is implanted within a patient. Optionally, if desired, the housing 230 may terminate near the battery such that a portion of the battery housing is exposed, and may be used as electrode 220B, if desired.

To implant LCP 200 inside patient's body, an operator (e.g., a physician, clinician, etc.), may need to fix LCP 200 to the cardiac tissue of the patient's heart. To facilitate fixation, LCP 200 may include one or more anchors 224. Anchor 224 may be any one of a number of fixation or anchoring mechanisms. For example, anchor 224 may include one or more pins, staples, threads, screws, helix, tines, and/or the like. In some examples, although not shown, anchor 224 may include threads on its external surface that may run along at least a partial length of anchor 224. The threads may provide friction between the cardiac tissue and the anchor to help fix anchor 224 within the cardiac tissue. In other examples, anchor 224 may include other structures such as barbs, spikes, or the like to facilitate engagement with the surrounding cardiac tissue.

Figure 3:
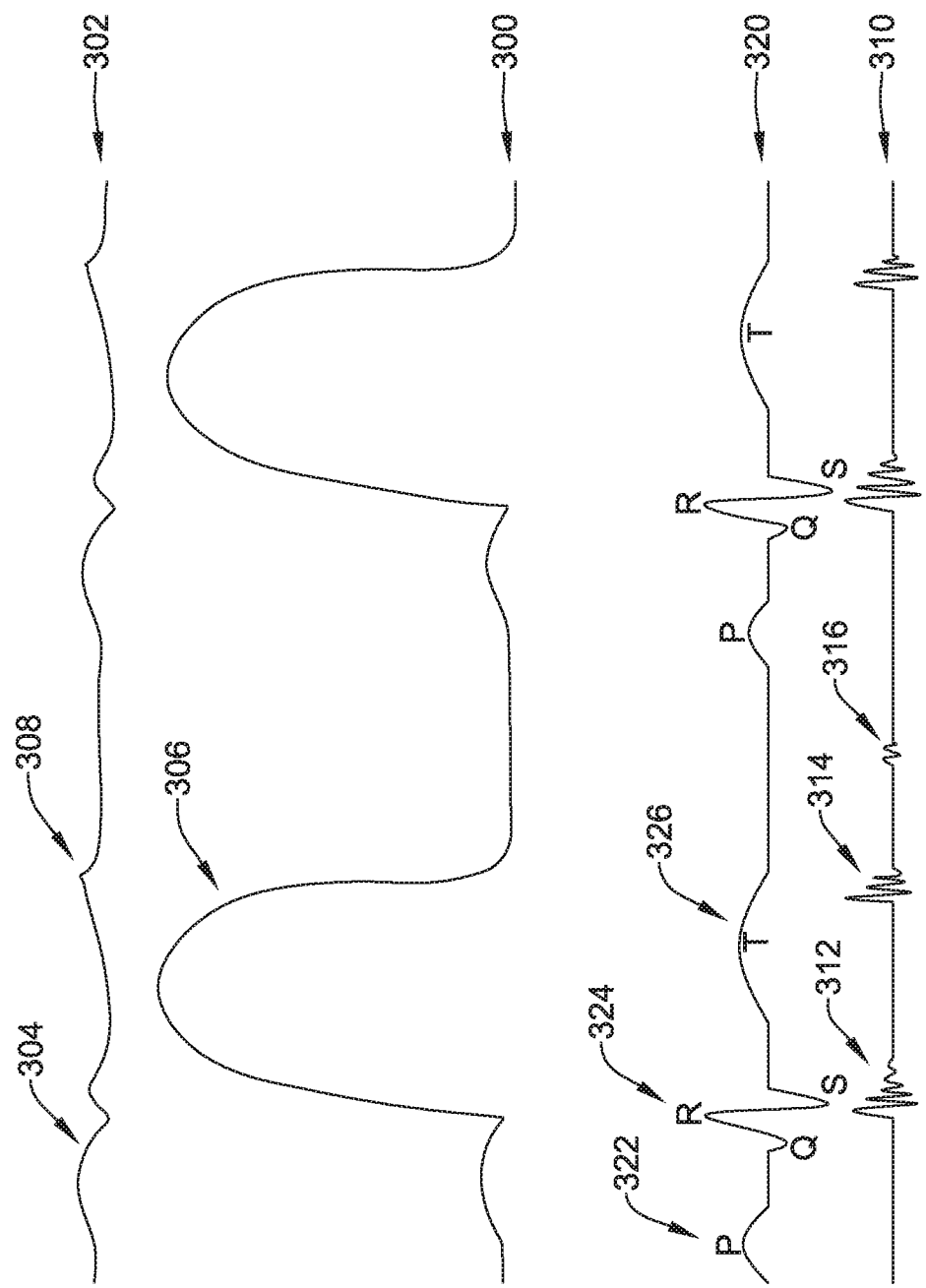
FIG. 3 illustrates acoustic, electrical and pressure waveforms that occur during a typical cardiac cycle.

FIG. 3 illustrates acoustic, electrical and pressure waveforms that occur during a typical cardiac cycle. The ventricular pressure is shown at 300, and atrial pressure is shown at 302. A phonocardiogram is shown at 310, illustrating the heart sounds that would be detected by the same "pressure" sensor as one of the pressure traces shown at 300, 302. The phonocardiogram is shown as reflecting each of a first heart sound 312, second heart sound 314, and third heart sound 316. Those skilled in the art recognize that the first, second and third heart sounds 312, 314, 316 are in fact terms of art.

The electrocardiogram is shown at 320, including well known P-Q-R-S-T wave sequences as the heart beats. These "waves" represent the electrical signals that flow through the myocardium to trigger muscle contractions during depolarization and subsequent repolarization. Thus, the P-wave 322 represents atrial depolarization, the R-wave 324 represents ventricular depolarization, and the T-wave 326 represents ventricular repolarization.

As can be seen, the P-wave 322 corresponds to a change 304 in the atrial pressure 302, though atrial pressure changes are much smaller than those of the ventricles. Next, the R-wave 324 temporally corresponds to the first heart sound 312, as the atrioventricular valves (tricuspid and mitral) close at the start of ventricular depolarization. As the ventricles contract in response to depolarization, the ventricular pressure increases as illustrated at 306, and the contraction continues until the muscle begins to relax and ventricular pressure drops. The aortic and pulmonary valves close causing the second heart sound 314. Atrial pressure shows a small notch (the dichrotic notch) at the closure of the aortic valve, as shown at 308. The third heart sound 316 is thought to possibly correspond to the refilling of the heart chambers following a contraction.

Some prior art approaches to pacing capture verification rely primarily on the electrical signals generated by the heart. Presence of an R-wave at a specific time, or having a specific morphology (shape), can be detected to confirm that a therapeutic pacing pulse has had its intended effect. Using an electrical signal, however, can be challenging if one or more of the sensing electrodes are also used for therapy, as the issuance of a pacing pulse can leave the electrode polarized, electrically, and blinded to responsive cardiac activity. Typically the electrode used to deliver a pacing pulse may be blanked, or cut-off, relative to sensing circuitry during and following the pacing pulse delivery. In addition, for an LCP, simplicity of design is paramount, as the size of the device is constrained by the need to deliver it to the heart through the vasculature and then leave it in the heart chamber. For example, some prior solutions may use non-pacing electrodes for capture verification signal detection, however, some LCP hardware embodiments may have only two electrodes, making this solution unworkable. Alternatives that use a non-electrical signal either as a primary source for capture verification, or to adjudicate other capture verification methods when those other methods fail to yield definitive results, are desired.

The inventors have recognized that a pressure sensor or sensors may be added to the LCP hardware and used for capture verification. An illustrative pressure sensor may take the form of a piezo-resistive micro-machined silicon sensor with an integrated pressure reference element. In some cases the sensor may be of a capacitive sensing type. These types of sensors may be deployed in distinct compartments of an implantable device with compliant interface to the blood pool or tissue environment that provides a gas and liquid tight barrier whilst allowing the transfer of pressure waves. The interior of the pressure sense compartment may be fluid filled for efficient transfer of pressure. Alternate pressure sensors may be realized by the integration of strain gages to the wall(s) of the implantable device housing. A variety of implementations are possible.

The use of pressure signals for capture verification may be of particular use for systems having an LCP placed in the left ventricle (such as shown at 104 in FIG. 1), where the pressure swings will be greater and more immediate than in other chambers of the heart. However, the following methods may be applied for devices in other chambers as well. Capture verification may be performed as an ongoing process for each delivered paced beat. Alternatively, capture verification may be a periodic process used in conjunction with pace threshold testing in which the pacing threshold is reduced until capture is lost, in order to ensure that the output pacing therapy energy is well tailored to the patient over time.

Figure 4:
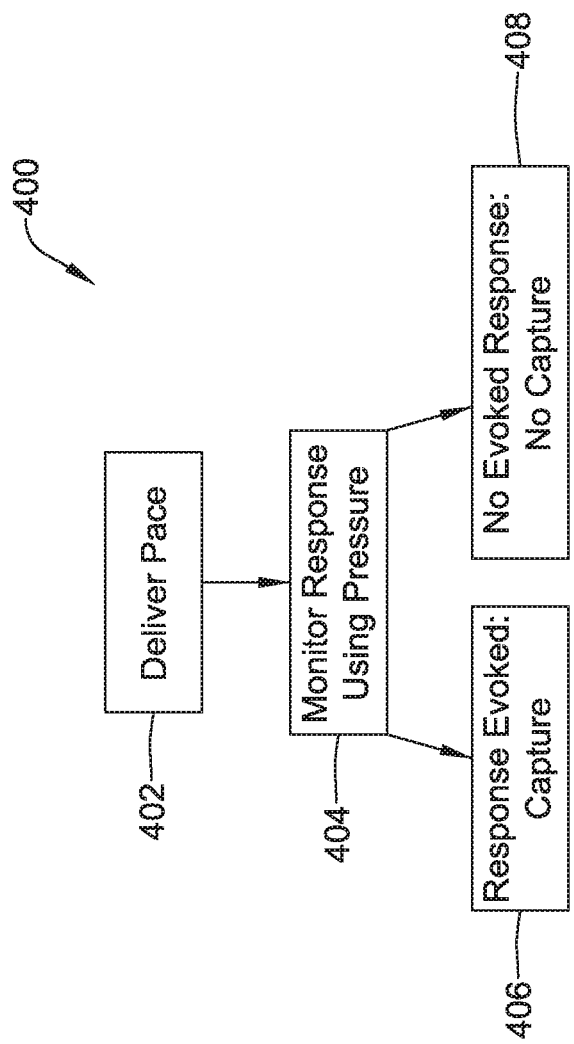
FIG. 4 shows an illustrative method in block flow format.

FIG. 4 shows an illustrative method in block flow format. The method 400 begins with delivery of a pacing pulse, as shown at 402. Next, the method comprises monitoring the cardiac response using pressure, as shown at 404. The sensed pressure is analyzed and the method either concludes that a desired response has been evoked, as noted at 406, or no evoked capture response has been observed, as shown at 408.

Figure 11:
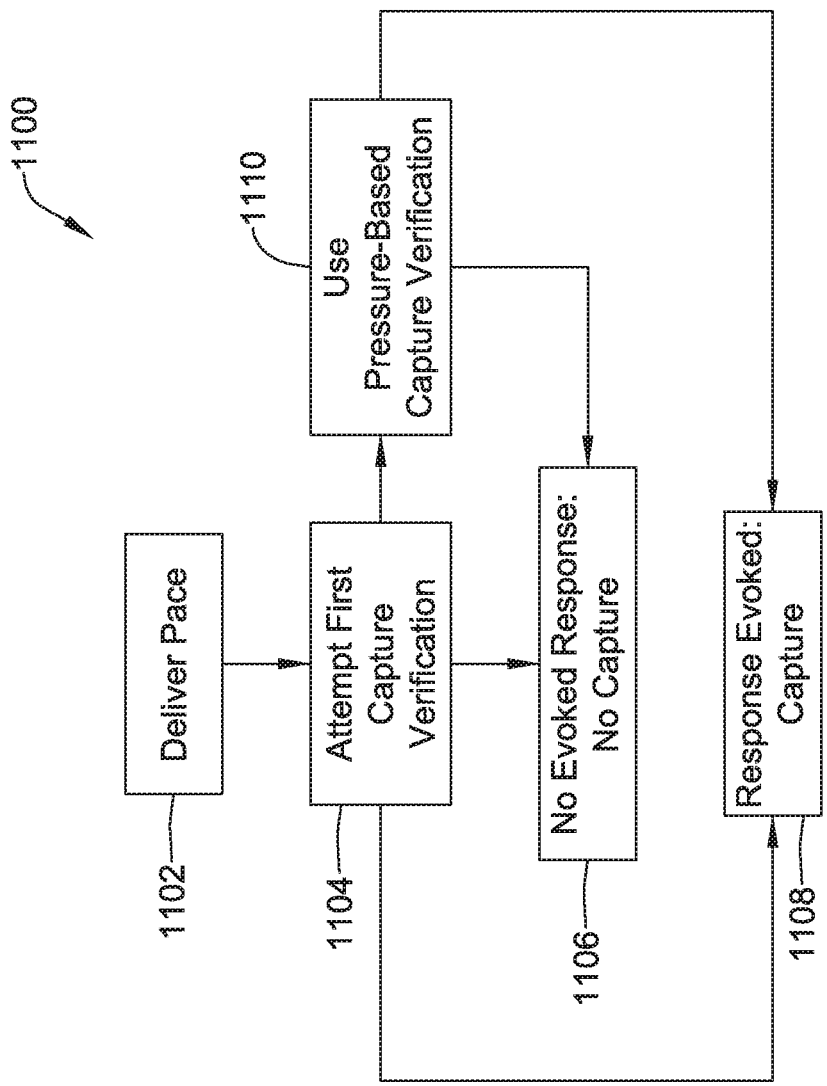

As illustrated in additional embodiments below, the analysis to yield either result 406 or 408 may include, for example, comparing detected pressure to a threshold. In other examples, the pressure waveform itself may be compared to a pressure waveform template, or the peak slope of pressure may be analyzed (possibly in combination with threshold checking). In other examples, the pressure signal may be analyzed to identify a fiducial pressure event (maximum positive or negative slope or peak, for example), and determining an interval between the fiducial pressure event and one or more of an acoustic or electrical event, or the timing of pace delivery, and then analyzing the interval to determine whether capture has taken place. In some examples, the method of FIG. 4 may be combined with a second capture verification method, as illustrated in FIG. 11, below.

Reviewing the method in some further detail, block 402 may reflect the delivery of a pacing pulse at the expiration of a timer, sometimes referred to as expiration of an escape interval. For example, in bradycardia pacing, the escape interval defines a minimum cardiac rate that is to be allowed. Block 404 may include taking a series of samples of the pressure signal at, for example, a frequency in the range of about 25 Hertz to about 500 Hertz, or higher or lower. The pressure signal may be monitored during a time period of interest, for example, starting at or within up to 250 milliseconds after the delivery of a pacing pulse, with pressure signal being captured for as little as 50 milliseconds of time up to about 600 milliseconds. In an example, the pressure signal may be captured at a 100 Hz sampling rate for 400 milliseconds following delivery of the pacing pulse. In an adaptive method, the typical timing of a patient's cardiac response may be observed (see FIGS. 5B and 6B for some initialization concepts), and windowing of the sampling may be narrowed to those time periods of greatest interest, in order to preserve current in the battery powered system. In the event that no evoked capture response is observed, as indicated at 408, the system may keep pacing parameters fixed until a pattern of failure to capture is observed or, alternatively, the system may change pacing parameters using one or more of the steps illustrated below in FIG. 12.

Figure 5A:
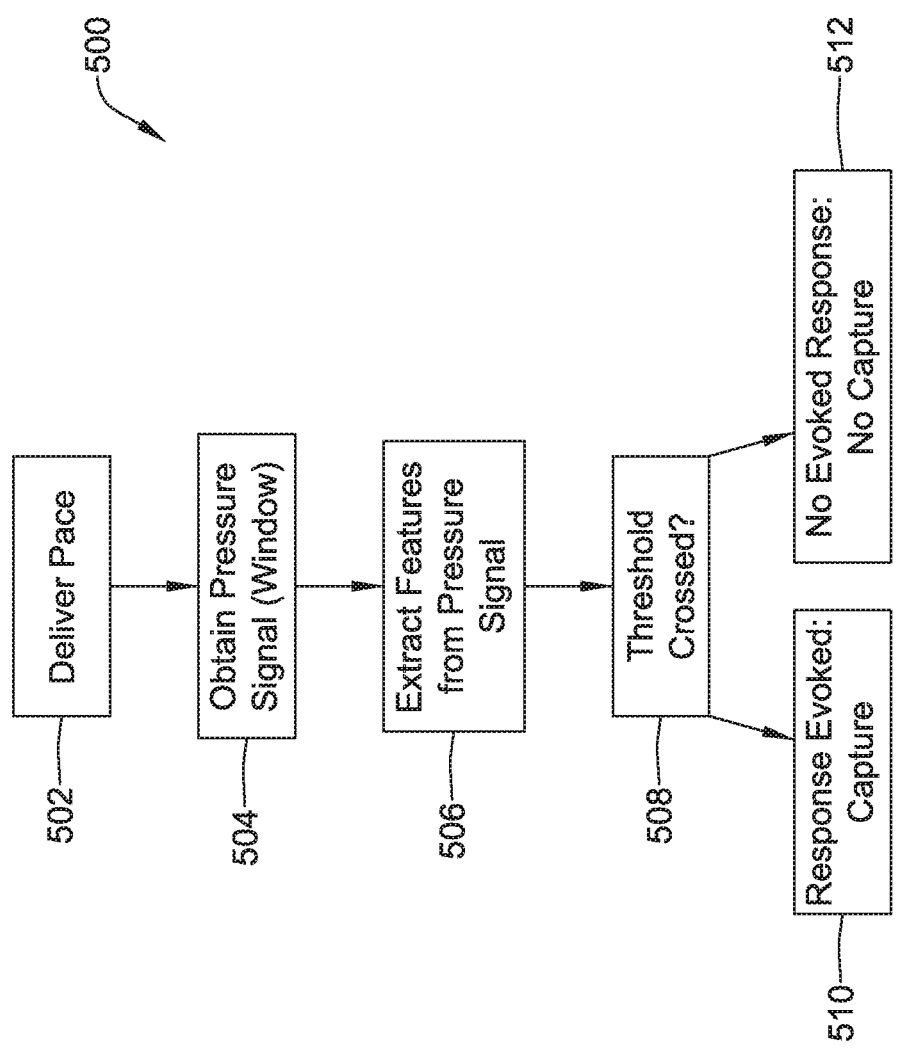
FIG. 5A shows an illustrative method in block flow format.

FIG. 5A shows an illustrative method in block flow format. The method 500 begins with delivery of a pacing pulse 502. Next, a pressure signal is captured, as indicated at 504; pressure signal capture 504 may be narrowed to a particular window of time, as desired. A feature is extracted from the pressure signal, as shown at 506. A number of different features may be extracted. For example, a pressure peak or minimum may be tracked. In an illustrative example, the feature may be the peak pressure during systole, or diastole, or overall during a window following pace delivery. In another illustrative example, the feature may be the minimum pressure during diastole, or during systole, or overall during a window following pace delivery. In another illustrative example, the feature may be the peak rate of change of pressure, during one of systole or diastole, or overall during a window following pace delivery. In another example, the feature may be the minimum rate of change of pressure during diastole, or during systole, or during a window following pace delivery. A plurality of features may be extracted and compared to different thresholds, if desired, with pacing capture verified if some, a majority, or all of the features exceed corresponding thresholds.

It is next determined whether a feature threshold is crossed, as shown at 508. If the feature threshold is crossed, the method concludes that the desired response has been evoked, as indicated at 510 or, if not, finding instead that no evoked capture response took place and so no capture occurred 512.

Block 508 may take several approaches to "threshold" crossing depending on the selected feature. In one example, the threshold crossing may be as simple as determining whether the pressure crossed some absolute threshold, or showed some total change from a first time (such as at the time pacing pulse was delivered) to a peak in the sensed window. In an example, the threshold must also be crossed for at least a predetermined period of time (for example, 50 to 300 milliseconds, or more or less) to be deemed a threshold crossing at 508 indicating that an evoked capture response has occurred. In another example, the threshold analysis may include calculating the area over a threshold encompassed by the signal—that is, how much over the threshold multiplied by show long the signal remains over the threshold.

Figure 5B:
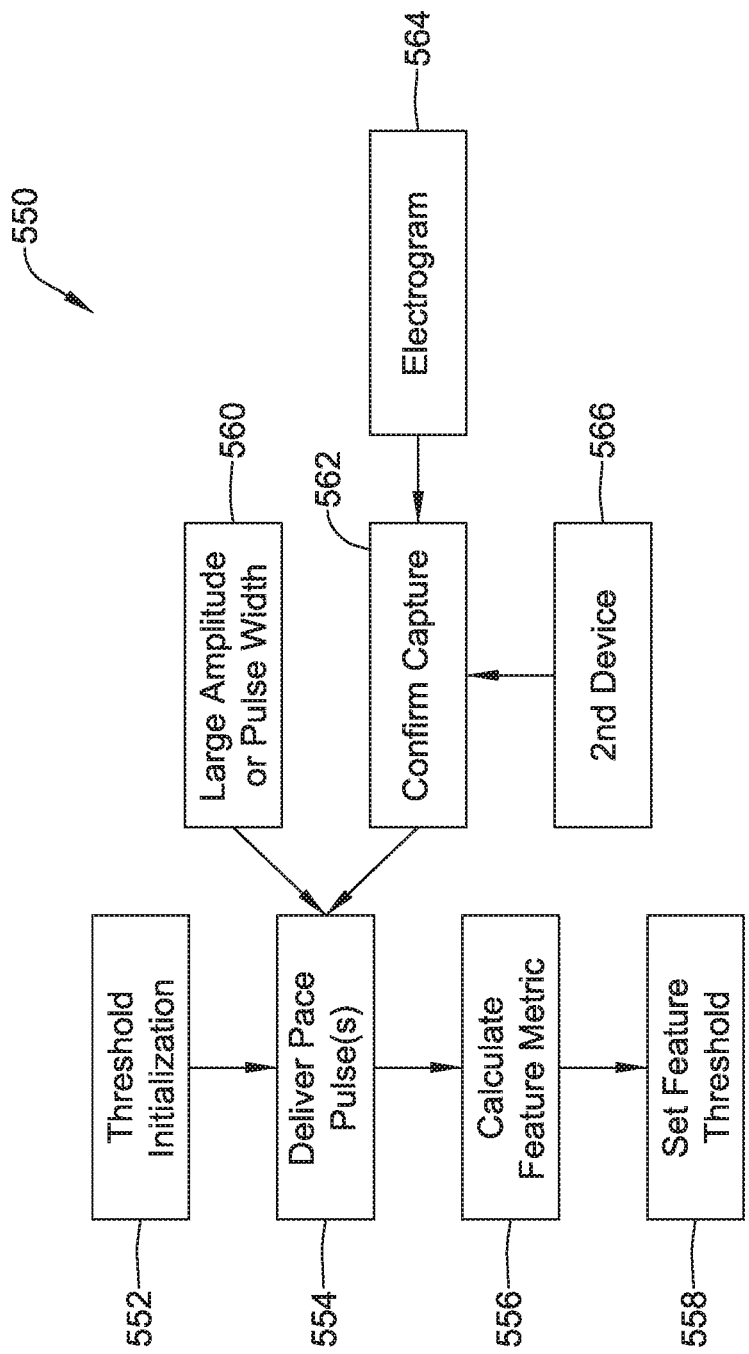
FIG. 5B shows an illustrative initialization method for use with the method of FIG. 5A.

FIG. 5B shows an illustrative initialization method for use with the method of FIG. 5A. The initialization process 550 comprises selecting a step for threshold initialization 552. Threshold initialization 552 may be called, for example, periodically (i.e. once an hour, once a day, once a week, etc.), or occasionally in response to an event. For example, threshold initialization 552 may take place at clinical follow-ups. Threshold initialization 552 may take place in response to a change in pacing parameters.

Threshold initialization 552 may also take place in response to detection of a change in patient activity, posture, respiratory rate, heart rate, cardiac arrhythmia status, sleep status, or a body chemical or other physiological parameter.

For example, an accelerometer may also be provided in an LCP in order to detect activity or posture changes by the patient. When the accelerometer indicates changes in activity or posture, the threshold initialization 552 may be called.

Initialization 552 may also be called in response to a detected cardiac condition, for example, if the patient endures bouts of atrial fibrillation, the identification that atrial fibrillation is ongoing (by the self-same or a second device such as an atrial LCP, or subcutaneous monitor or defibrillator, or a transvenous pacemaker, defibrillator or cardiac resynchronization device) may trigger initialization 552.

In another example, threshold initialization 552 may occur in response to the patient's respiratory status. For example, a thoracic impedance sensor may be provided to detect respiratory parameters such as respiratory rate, tidal volume and minute ventilation. In this illustrative example, initialization 552 may also be called if a respiratory parameter changes beyond a predetermined threshold.

In another example, a patient's sleep status may be determined and may prompt threshold initialization. Sleep status may be determined by, for example, observing a prolonged period of inactivity or lack of motion, or using methods described in U.S. Pat. No. 7,189,204, titled SLEEP DETECTION USING AN ADJUSTABLE THRESHOLD, the disclosure of which is incorporated herein by reference. Threshold initialization may occur when the sleep state is entered, and/or may be performed (again) if it is determined that the patient has awoken.

In another example, the patient's body chemicals may be monitored or observed and a change in chemical state may trigger threshold initialization 552; monitoring of body chemicals maybe performed as described in U.S. Pat. No. 7,809,441, titled IMPLANTABLE MEDICAL DEVICE WITH CHEMICAL SENSOR AND RELATED METHODS, the disclosure of which is incorporated herein by reference. For example, conditions such as heart failure can cause body chemicals, in particular electrolytes such as potassium, to markedly change. A chemical sensor may detect when a threshold for a particular chemical, such as an electrolyte, for example, potassium, is crossed, and this may prompt threshold initialization. Initialization 552 may also be called if conditions such as hypokalemia or hyperkalemia are detected.

During the initialization routine, one or a plurality of pacing pulses are delivered, as shown at 554, and the relevant pressure threshold metric is calculated for the delivered pace pulse(s). The relevant pressure threshold metric may be any of the examples noted above, such as absolute peak (within a window if desired). In other examples, the metric may have multiple parts, for example, if the rule to be initialized relates to time over threshold, or area of the curve over a threshold, the time or area can be set, or the threshold can be set, or both. The evoked pressure threshold(s) are then set, as indicated at 558, and may be used in the methods shown in FIG. 5A, or in other methods shown herein.

In an example, the maximum pressure peak is found at block 556 for a set of anywhere from one to ten pace captured cardiac contractions, and the threshold at 558 is set to be in the range of about 50% up to about 95% of the average or median maximum pressure peak(s). This threshold may be used as an absolute threshold. Alternatively, this first threshold can be used to then determine the area of the curve over the threshold for the one to ten pace captured contractions, to generate a median or average are of the curve over the now set threshold. Capture verification parameters can then be set from the area over the curve relative to the set/calculated threshold using, for example, a percentage or statistically derived parameter (such as by calculating standard deviation or variance) away from peak, median or average values.

To facilitate the initialization method 550, the pace pulses delivered at 554 may be delivered with parameters, such as amplitude and/or pulse width, that are selected to give a high likelihood of actual capture, as indicated at 560. Alternatively, capture may be confirmed for each of the pace pulses delivered during block 554, as indicated at 562. Confirmation may use, for example the cardiac electrogram as indicated at 564, or by using data received from a second device that is observing the initialization process, as indicated at 566. For example, if an LV-placed LCP is performing the initialization process 550, a separate implanted device may communicate with the LCP to confirm capture is occurring, with the second device being, for example, another LCP in the RV or an atrial chamber, or a subcutaneous cardiac monitor or defibrillator, or a transvenous pacemaker, defibrillator or resynchronization device.

Figure 6A:
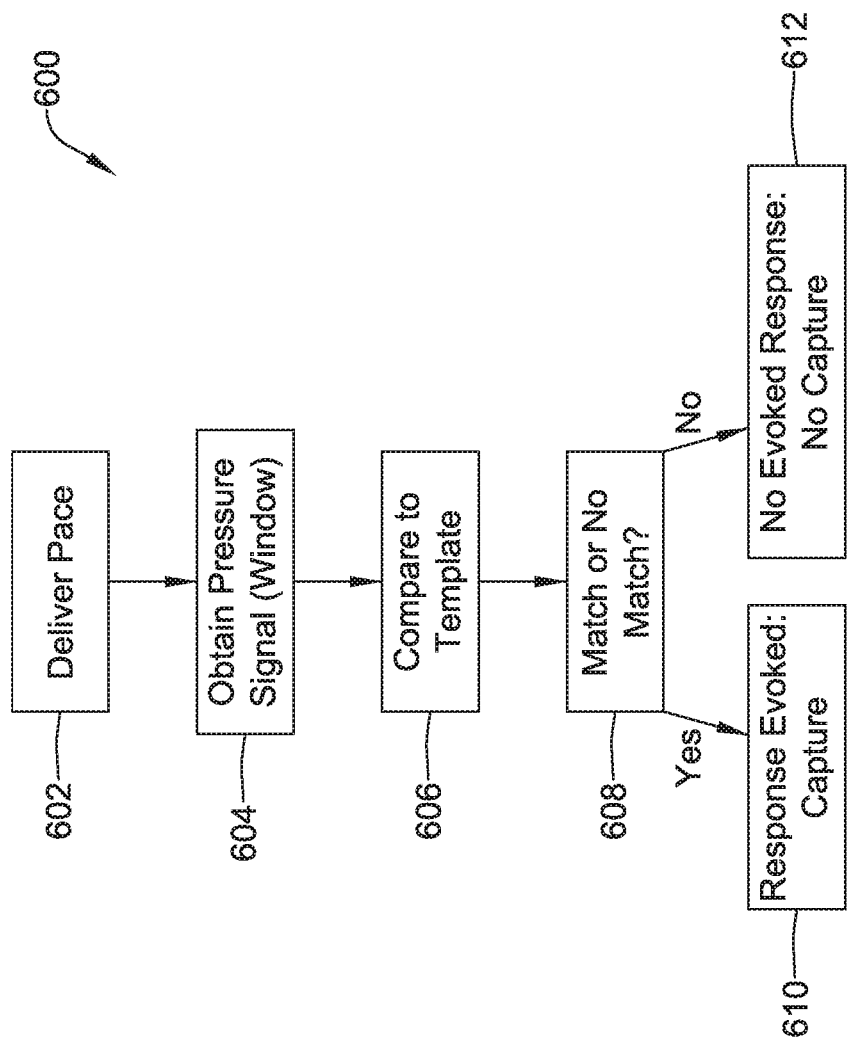
FIG. 6A shows an illustrative method in block flow format.

FIG. 6A shows an illustrative method in block flow format. In this example, the pressure-based capture verification 600 comprises delivering a pacing pulse at 602. A pressure signal across a window of time is then obtained at 604. The obtained pressure signal is then compared to a template, as shown at 606, at it is determined whether a template match occurs, as shown at 608. If the template is matched, then it is concluded that a response was evoked and capture is confirmed, at 610. If the template is not matched, then it is found that the desired response was not evoked, and capture cannot be confirmed, as indicated at 612.

To perform comparison to a template, one of several alignment methods may be used. In one example, the entire obtained signal is compared using, for example, correlation waveform analysis (CW) and/or a simplified CWA using a difference of area analysis. Wavelet, principal component analysis or other more complex approach may be used; however, the most likely approach would simply be a difference of area analysis. In another example, the template may be calculated to have a fiducial point, for example a peak at the start or end thereof, or at a maximum slope point, with the fiducial point being also identified within the obtained pressure signal from block 604 and used to align the template and obtained pressure signal to allow comparison. In yet another example, the comparison process may be performed repeatedly to identify a "best match" between the obtained pressure signal and the template. Template matching may be combined with a pressure feature analysis as shown by FIG. 5A, for example, calling for both a template match and at least a pressure amplitude feature or pressure slope feature to exceed a threshold, in order to verify pacing capture.

Figure 6B:
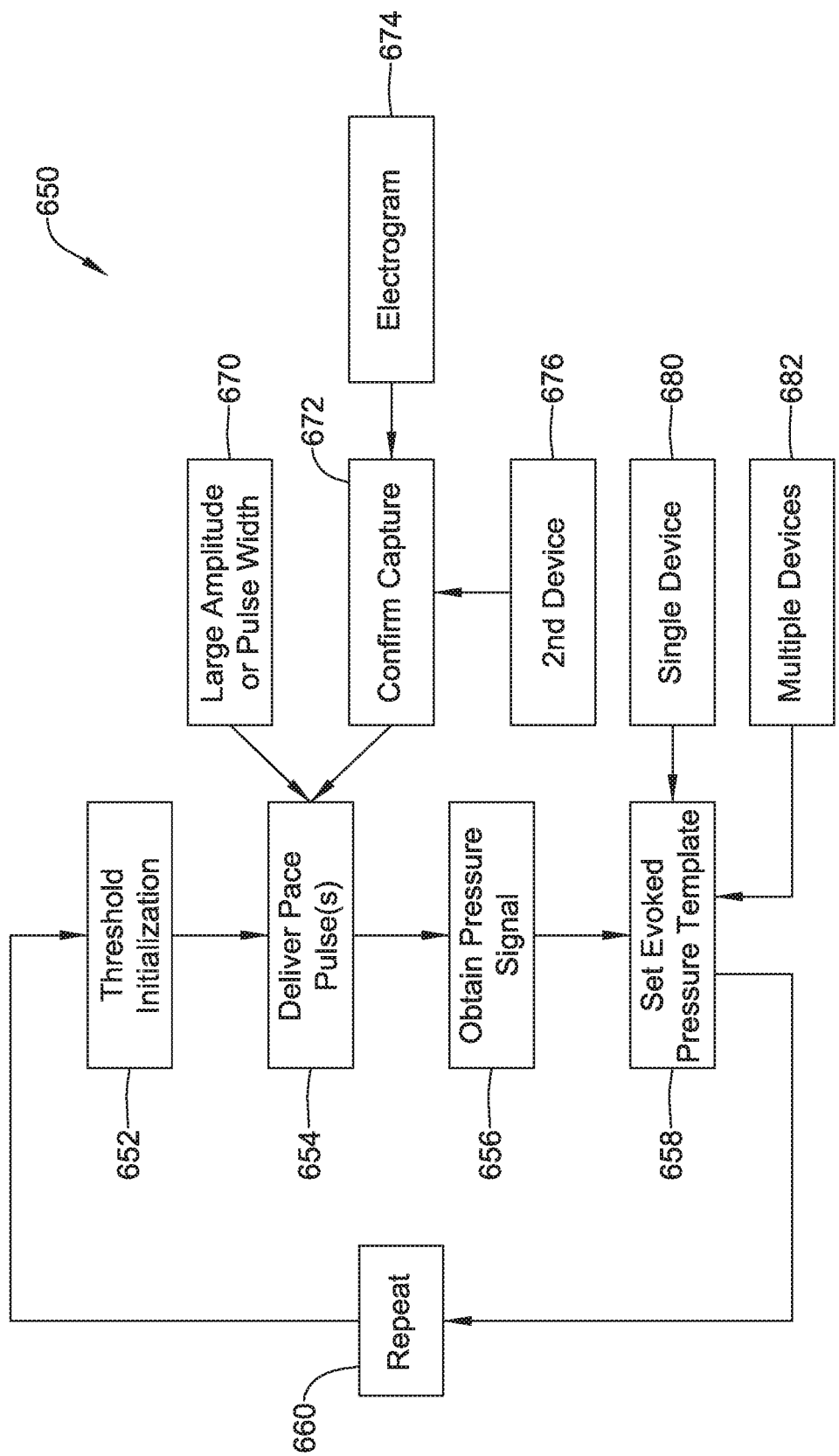
FIG. 6B shows an illustrative initialization method for use with the method of FIG. 6A.
Figure 7:
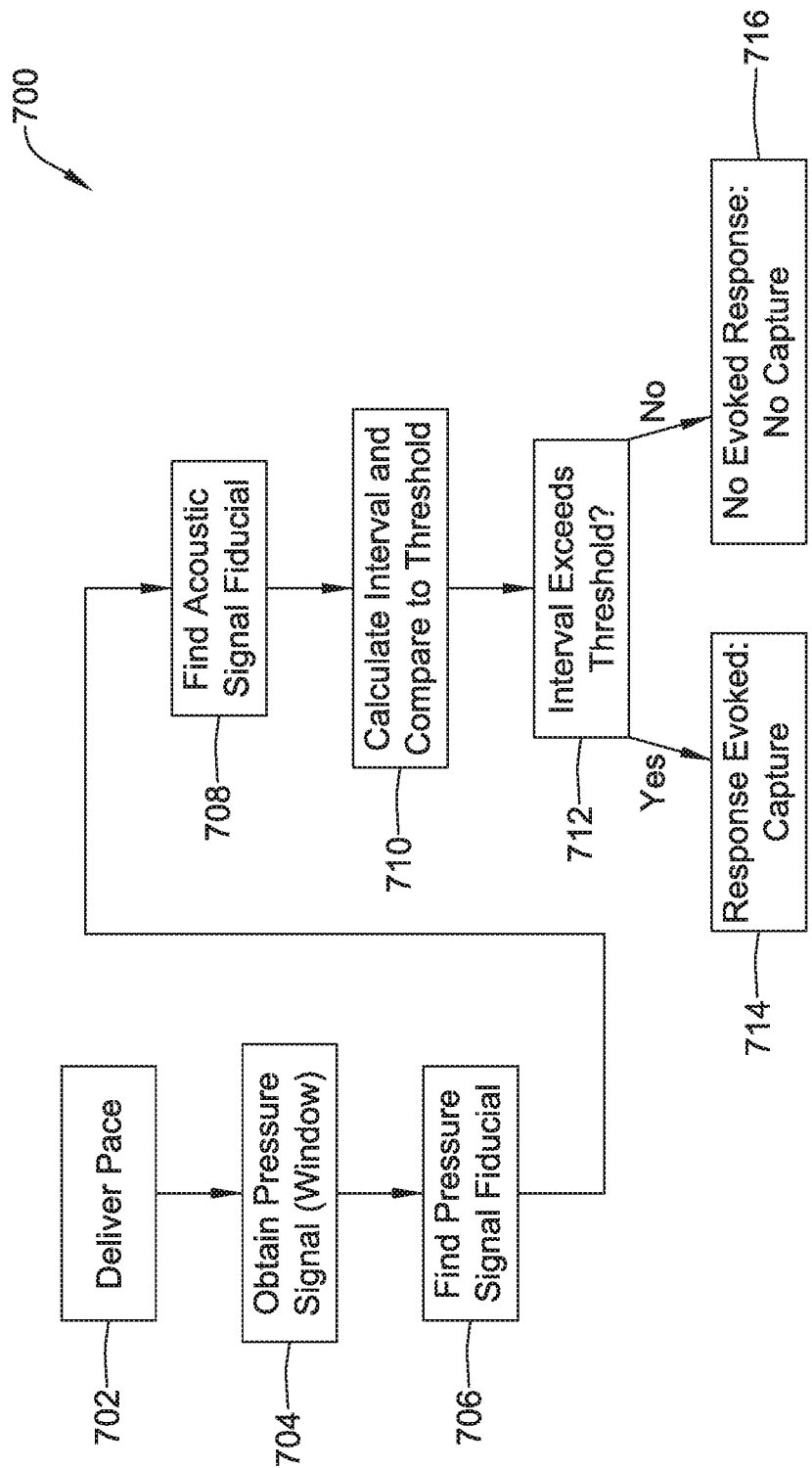
FIGS. 7-12 shows illustrative methods in block flow form.

FIG. 6B shows an illustrative initialization method for use with the method of FIG. 6A. The process 650 begins with an initialization call, as indicated at 652. As with initialization routines shown at FIG. 5B, initialization call 652 may be periodic or occasional, using any of the examples already noted above for periodic and/or occasional (re)-initialization. One or more pacing pulses are then delivered, as indicated at 654. Again, step 654 (much like in FIG. 5B) may use large amplitude or pulse width pacing pulses 670 to ensure capture, and/or may confirm capture 672 using the cardiac electrogram 674 and/or a second device 676.

Pressure signal(s) are obtained at 656 for each of the one or more pace pulses delivered in 654. The obtained signals may be continuous throughout the pacing time period or may be limited to a window or windows of interest, using sampling rates and window sizes/durations already described above in reference to FIG. 5B. In an example, the sampling rate for a template formation initialization shown in FIG. 6B may be higher than the standard sampling rate used for pressure signals in the actual beat-to-beat capture verification analysis of FIG. 6A (or other verification analyses described herein). The obtained signals can be referred to as obtained pressure template formation signals.

Next, an evoked pressure template is set, as indicated at 658. Template setting may include any of a variety of processes including, for example and without limitation:

Identifying, by use of peaks, peak slopes, inflection points, or threshold crossings, for example, a fiducial point for alignment of obtained pressure template formation signals, or for alignment to be used during the capture verification process Averaging plural obtained pressure template formation signals Performing principal component analysis or wavelet transform analysis on one or plural obtained pressure template formation signals Defining a signal window of interest for the obtained pressure template formations signals and using this signal window to define the pressure signals to be obtained during capture verification processes Templates may be separately formed for each of cardiac capture and non-capture, if desired. In one example, an obtained pressure signal can be compared against each of a template for capture and a template for non-capture, and if the obtained pressure signal is more similar to the template for capture, then the pace pulse is deemed to have captured the heart. In another example, only a template for capture exists, and a threshold is set to determine whether an obtained pressure signal "matches" the template sufficiently to support a conclusion that capture took place. In another example, only a template for non-capture exists, and a threshold is set to determine whether an obtained pressure signal matches the template sufficiently to support a conclusion that no capture occurred.

The formation of templates may be done for a single device as indicated at 680 by creating a single template. On the other hand, if desired, a plurality of templates may be formed for plural patient postures (standing, seated, laying down, etc.), using, if desired, an output of an accelerometer to indicate what posture the patient is in or, in a directed method, using a set of postures that the patient is instructed to adopt by the use of an external device such as a home monitoring device, clinician programmer, or connected smartphone, for example, in which the external tells the patient to hold a particular posture and then indicates that the implant may perform a data gathering procedure. The process may be repeated 660 to account for additional postures, or for different patient activities (sleeping versus exercising, for example). If a patient is prone to certain conditions such as atrial fibrillation, the process may be repeated with and without atrial fibrillation ongoing. In a multiple device context 682, more than one template may be formed to account for different full and partial capture or non-capture modes. For example, if LCP devices are in each of the left and right ventricle, multiple templates maybe formed including two or more of the following:

Left LCP capture; Right LCP capture; (double capture)
Left LCP capture; but no Right LCP capture; (single capture—left)
Right LCP capture; but no Left LCP capture; (single capture—right)
Neither Left nor Right LCP captured (no capture)

Coordination of the Left LCP and Right LCP can be used to facilitate the process by, for example, having one device withhold therapy while the other delivers therapy to obtain templates for the single-capture conditions, with both devices delivering therapy for the double capture condition and both withholding to obtain the no capture condition, and repeating for those 660. It may be useful to have two or more such templates, though not all may be needed in a given usage.

FIGS. 7-12 shows illustrative methods in block flow form. The method 700 in FIG. 7 uses two separate pressure-sensor derived signals. A pacing pulse is delivered at 702, and the pressure signal is obtained at 704 and processed, in one example, through two channels for higher frequency acoustic content and lower frequency pressure content. A pressure signal fiducial point is identified at 706, such as the peak ventricular pressure, maximum upward slope, or an inflection point, initial threshold crossing, or pressure change, and a timing marker created for the pressure signal fiducial point. An acoustic signal fiducial is identified at 708 such as, for example, the first or second heart sounds (See FIG. 3).

A time interval between the pressure signal fiducial 706 and the acoustic signal fiducial 708 is calculated, and compared to a threshold. For example, the interval may be from the upward excursion of the pressure signal, or max peak point of the upward rise of pressure, or the inflection point indicating that the upward slope of the pressure signal is starting to decrease, to the second heart sound. This time interval is then compared to a threshold, as indicated at 710. If the time interval exceeds the threshold at 712, then an evoked capture response is found and capture has taken place as indicated at 714. If the time interval does not exceed the threshold, then the cardiac response that has been measured is not the evoked capture response that was intended, as indicated at 716, and no capture is found to have occurred. The interval threshold used in block 712 may be set using a known value, or an assumption, or it may be calculated using a method such as those of either FIG. 5B or FIG. 6B.

Figure 8:
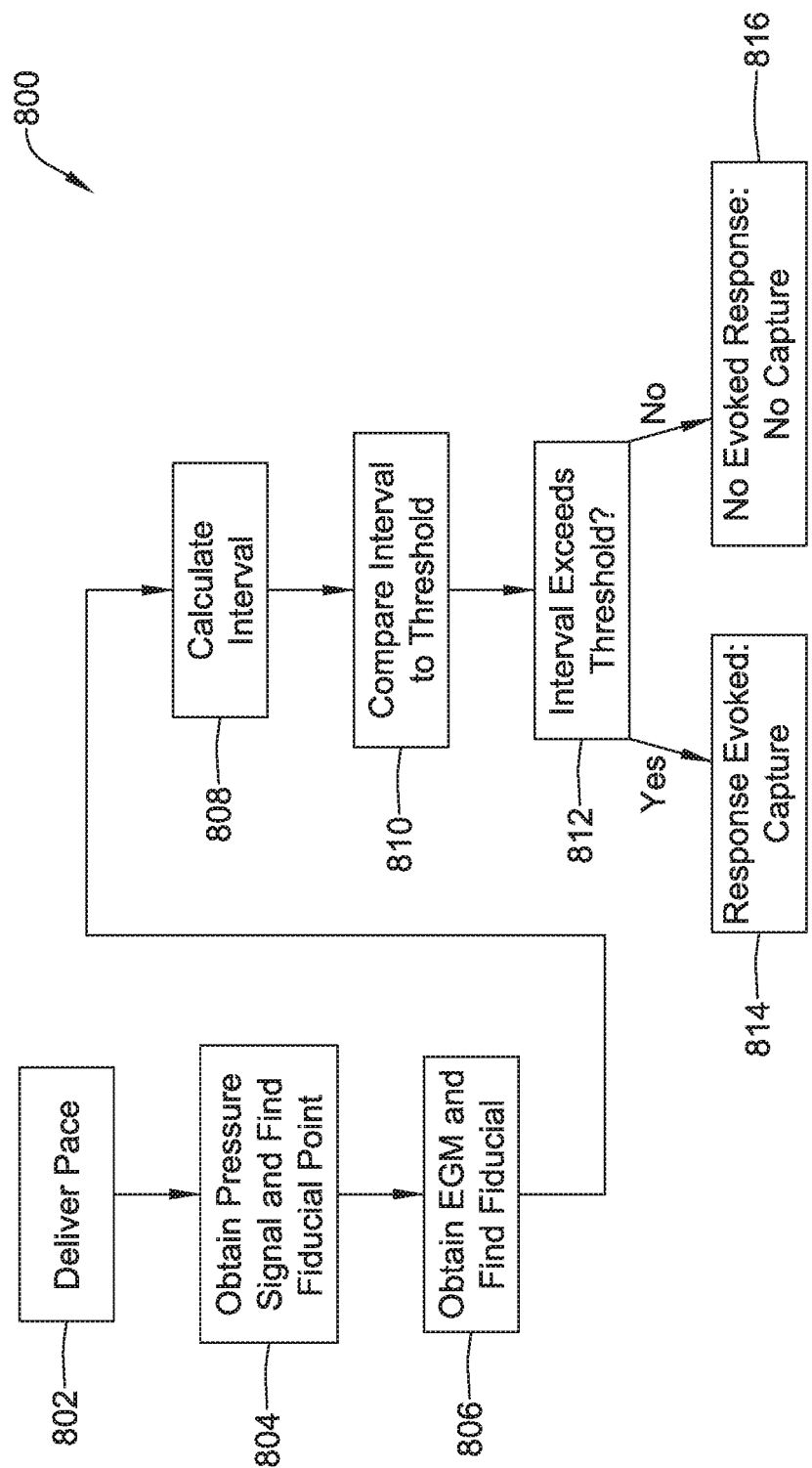

FIG. 8 shows another example method. In FIG. 8, method 800 uses both an electrogram based signal and a pressure signal to perform capture verification. Again the method begins with delivery of a pacing pulse at 802, followed by obtaining a pressure signal at 804, with a pressure fiducial point identified in the pressure signal 804. The fiducial point may be a maximum, minimum, inflection point, maximum slope point, threshold crossing or other identifiable predefined event of the pressure signal. The method next obtains the electrogram (EGM) occurring before, during and/or after the pace signal, as indicated at 806, and identifies another fiducial point. For example, the EGM fiducial may be an R-wave peak, or P-wave, or a QRS onset, or a turning point or inflection point associated with any of these signals, and the pressure fiducial may be the time at which a peak pressure occurs, or pressure dropoff begins, the dichrotic notch, or an inflection point occurs.

An interval is then calculated between the pressure fiducial and the EGM fiducial, as indicated at 808, and compared to a threshold as indicated at 810. The interval threshold used in block 810 may be set using a known value, or an assumption, or it may be calculated using a method such as those of either FIG. 5B or FIG. 6B. If the interval exceeds the threshold at 812, the method determines that the desired response has been evoked and capture took place, as indicated at 814. If the interval does not exceed the threshold at 816, the method concludes that the desired evoked capture response did not occur and capture did not take place. In one example, using the P-wave as an EGM fiducial point and a fiducial point of the pressure signal (e.g. dichrotic notch), if the interval is shorter than that during intrinsic beats by a threshold amount, it is determined that the LV is captured, if not, it is determined that the LV is not captured.

Figure 9:
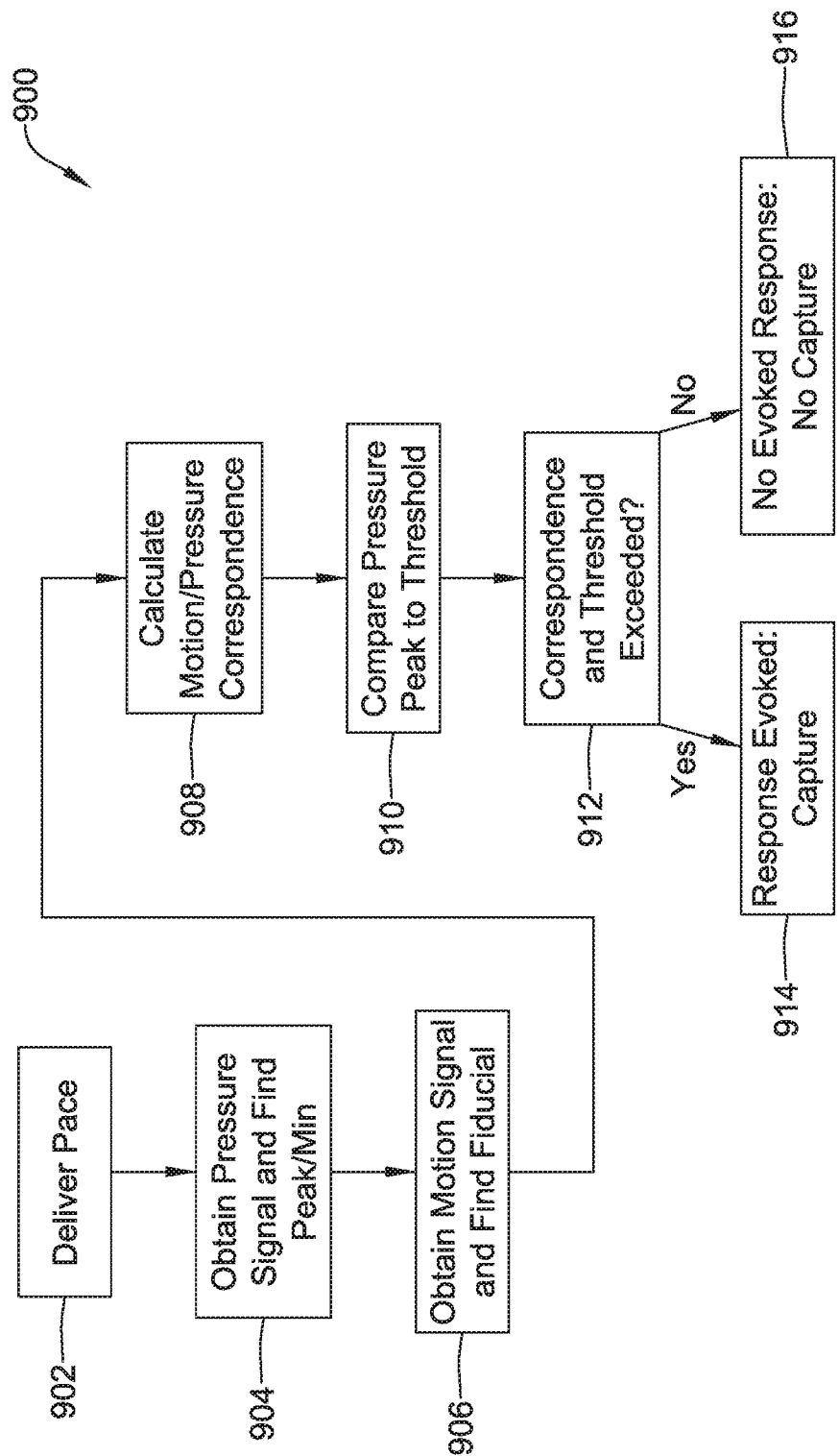

FIG. 9 shows another example method. In FIG. 9, the method 900 uses both a pressure based signal and a motion signal to perform capture verification. Again the method begins with delivery of a pacing pulse at 902, followed by obtaining a pressure signal at 904, with a pressure fiducial point identified in the pressure signal 904. The fiducial point may be a maximum, minimum, inflection point, maximum slope point, threshold crossing or other identifiable predefined event of the pressure signal.

Next, at 906, a motion signal is captured, and another fiducial is identified in the motion signal. For example, a fiducial may be an indication of movement of the cardiac muscle wall during contraction. As indicated at 908, the method next calculates a correspondence of the motion and pressure fiducial points—that is, did the pressure change correspond to the movement of the cardiac wall, for example, by occurring at approximately the same time the movement was detected, plus or minus a margin of up to 100 milliseconds. As a second check, optionally, block 910 also calls for determining whether the pressure signal exceeded a threshold, which may encompass any of the methods to "threshold" comparison discussed in reference to FIG. 5A, above. If both the correspondence at 908 and threshold at 910 are met, as indicated at 912, then it is determined that the desired cardiac response was evoked and capture took place, as indicated at 914. If either the correspondence or threshold checks are not met, the method concludes that the desired evoked capture response did not take place and capture did not occur, as indicated at 916.

Figure 10:
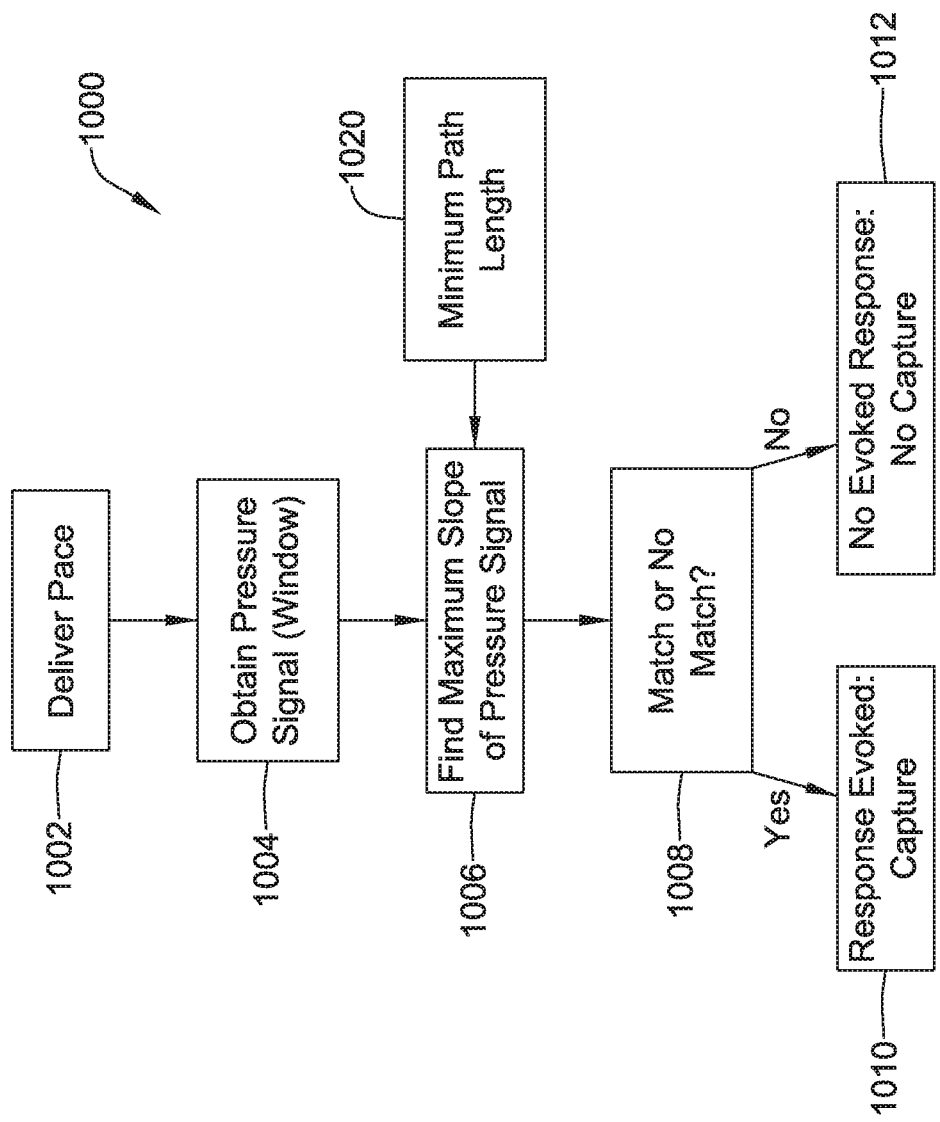

FIG. 10 shows another example. In this method 1000, a pace is delivered at 1002, and the pressure signal is again obtained as indicated at 1004. A maximum slope of the pressure signal is obtained as indicated at 1006. The maximum slope is then compared to a set of boundary conditions, as indicated at 1008, to determine if the maximum slope matches expectations and falls within a range having high and low borders. Alternatively, the applied range may only have a high boundary, or only a low boundary. If expectations at 1008 are met, the method determines that the desired cardiac response was evoked and capture took place, as indicated at 1010. If expectations at 1008 are not met, the method determines that the desired evoked capture response did not take place and capture did not occur, as indicated at 1012.

To ensure that the "maximum slope" is related to the desired signal type, a path length limitation may apply as indicated at 1020. For example, the path length minimum may require that the maximum slope be measured across a relatively long period of time, rather than a short spike that could be attributed to noise within the signal; for example, a minimum path length may require no turning points within 30 milliseconds before or after the "maximum slope" point. Thus the slope identified at 1006 would have to be within a 60 millisecond continuous upward slope, rather than reflecting a sudden spike. The path length rule 1020 is optional, and other approaches to eliminating noise or artifact from the pressure signal may be used.

FIG. 11 shows an example in which multiple capture verification processes are used. In the method 1100, a first attempt at capture verification is performed using a first process, for example, by analyzing the cardiac electrical signal by an LCP (using the EGM) or by a subcutaneous device using the subcutaneous electrocardiogram. The first attempt 1104 may deliver any of three outcomes:

Conclusively finding no evoked capture response and therefore no capture (1106)

Conclusively finding an evoked capture response and therefore capture (1108); or An inconclusive result, leading to the use of a pressure based capture verification 1110 for further adjudication between no evoked capture response 1106 or evoked capture response found 1108.

In an alternative approach, block 1104 and 1110 may be reversed, such that pressure-based capture verification is performed as a first attempt, with electrical cardiac signals, or a secondary device, used as the alternative to adjudicate inconclusive results. In another example, the device may select between blocks 1104 and 1110 based on one or more conditions of the patient and/or history of the patient such as using knowledge that a prior check of capture used one method was successful leading to a decision to keep using the same method for capture verification. In another example, a device may alternate between first and second (or third or more) capture verification methods.

Figure 12:
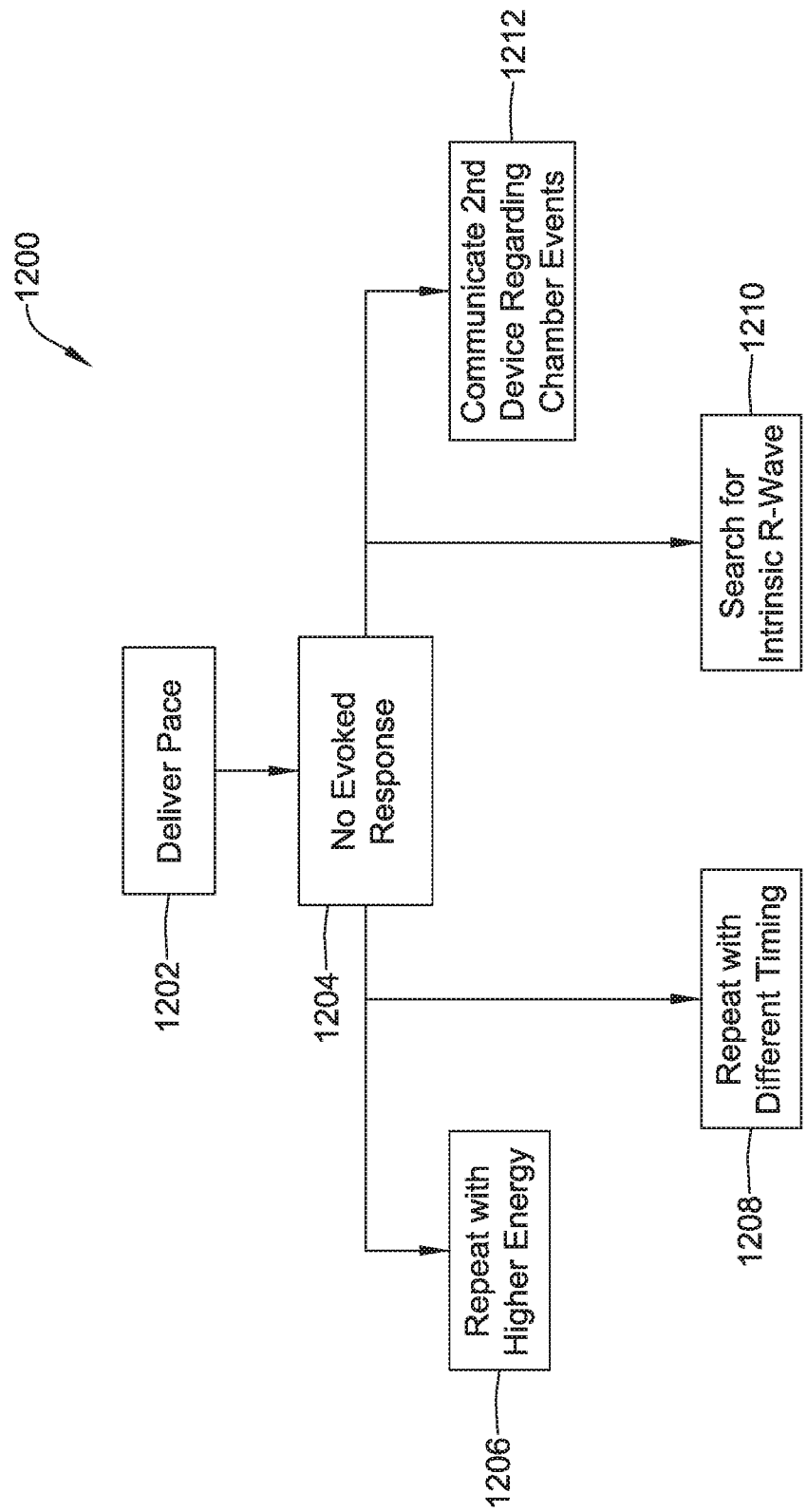

FIG. 12 illustrates a set of possible corrective actions or investigations that an implantable device may take in response to a failure to find an evoked capture response and verify capture. In method 1200, the pacing pulse is delivered at 1202, following by a finding of no evoked capture response at 1204. Corrective steps may be taken, including increasing the pace pulse energy level, at 1206, and/or changing the timing of pace therapy delivery 1208 by initiating sooner or delaying to a later time. Other corrective steps may include engaging in a search process to identify the intrinsic R-wave as indicated at 1210, using, for example, one or more of the cardiac electrical, acoustic, motion, or pressure signals. Another corrective step may include requesting data from a second device, as indicated at 1212, to determine the timing of various chamber events, for example, if capture did not occur for the LV or RV, it may be useful to determine whether and when contraction took place in other chambers including the other ventricle or the atria. Data from 1210 and 1212 may inform changes made in 1208, for example.

A device may be configured to take corrective action after a single iteration of block 1204, or may require a pattern. In one example, a device may automatically increase energy 1206 after a single iteration of block 1204, and may revert to the other items, 1208, 1210, 1212, in response to a pattern or trend of failed capture. Blocks 1208, 1210, 1212 may form part of a single, broader process.

Various Notes & Examples

Following are several illustrative examples provided to explain how various means may be used in some embodiments.

A first illustrative example takes the form of an implantable medical device (such as device 200 in FIG. 2) comprising: at least first and second electrodes (such as electrodes 220A, 200B, and 222) for at least one of delivering therapy or sensing electrical signals; a pressure sensor for sensing intracardiac pressure (such as a pressure or acoustic sensor 210); operational circuitry coupled to the electrodes and the pressure sensor (operational circuitry may include the processing module 212 and associated memory and logic circuits including, for example, analog to digital converters, digital to analog converters, logic arrays or gates, programmable arrays, a state machine, a microprocessor or microcontroller, or the like). The operational circuitry of this first illustrative example also includes pace means to deliver an electrical pacing stimulus to the heart of a patient using the at least first and second electrodes; monitor means to monitor for an evoked capture response indicating the electrical pacing stimulus was captured using the pressure sensor; and determining means to determine if the evoked capture response is detected and either: conclude that the electrical pacing stimulus captured at least a portion of the patient's heart; or conclude that the electrical pacing stimulus did not capture the patient's heart. The pace means may include the pacing output circuitry 204 of FIG. 2, which may include constant or varying current or voltage controlled circuitry such as a digital to analog converter, current mirror, voltage source, or other suitable circuitry, as well as coupling outputs such as DC blocking capacitor, and/or electrode selection circuits. The monitoring means may include operational instructions for execution by the processing module 212 to observe outputs of the pressure, acoustic sensor 210 over time, such as by use of block 404 in FIG. 4, block 504 in FIG. 5A, block 604 in FIG. 6A, block 704 in FIG. 7, block 804 in FIG. 8, block 904 in FIG. 9, and/or block 1004 in FIG. 10, for example. The determining means may include operational instructions for execution by the processing module for performing, for example, the analysis of blocks 406/408 of FIG. 4, blocks 508 and 510/512 of FIG. 5A, blocks 608 and 610/612 of FIG. 6A, blocks 712 and 714/716 of FIG. 7, blocks 812 and 814/816 of FIG. 8, blocks 912, and 914/916 of FIG. 9, and/or blocks 1008 and 1010/1012 of FIG. 10.

A second illustrative embodiment takes the form of a medical device as in the first illustrative embodiment, further comprising extracting means to monitor an output of the pressure sensor during a predetermined time period following operation of the pace means and extract a feature from the pressure signal; and comparing means to compare the extracted feature to a feature threshold and identify whether the feature threshold is exceeded; further wherein the determining means is configured to determine: that the evoked capture response has been detected if the comparing means find that the feature threshold is exceeded; and that the evoked capture response has not been detected if the comparing means finds that the feature threshold is not exceeded. Such an example is illustrated in FIG. 5A. In some variants of this second illustrative example, the extracted feature is a peak pressure during systole and the feature threshold is a pressure threshold; the extracted feature is a minimum pressure during diastole, and the feature threshold is a minimum pressure threshold for diastole; the extracted feature is a peak rate of change of pressure during systole, and the feature threshold is a minimum rate of change of pressure; the extracted feature is a minimum rate of change of pressure, and the feature threshold is a minimum rate of change of pressure; and/or the extracted feature is an area under the curve of a measured pressure over a period of time, and the feature threshold is a minimum area.

A third illustrative embodiment takes the form of a medical device as in the second illustrative embodiment, wherein the operational circuitry further comprises initialization means to initialize the feature threshold, wherein the initialization means comprises: therapy means to direct the pacing means to deliver one or more electrical pacing stimulus to the heart of the patient using the at least first and second electrodes using pacing parameters that are expected to capture the heart; calculating means to obtain signals from the pressure sensor and calculate an expected feature value using obtained pressure signals corresponding to evoked capture responses; and setting means to set the feature threshold in relation to the expected feature value. The therapy means may include operational instructions for execution by the processing module for using the pacing means, for example, as illustrated at block 554 of FIG. 5B and explained in association therewith. The calculating means may include operational instructions for execution by the processing module for performing, for example, as illustrated at 556 in FIG. 5B by obtaining signals from the pressure means (and or other sensors) and calculating the feature metric. The setting means may include operational instructions for execution by the processing module for performing, for example, as shown at 558 in FIG. 5B by, for example, setting a feature threshold in relation to a calculated metric.

A fourth illustrative example takes the form of a medical device as in the first illustrative example, wherein the monitor means comprises: extracting means to monitor an output of the pressure sensor during a predetermined time period following operation of the pace means and extract a set of pressure data from the pressure signal; and template matching means to determine whether the extracted set of pressure data matches an evoked pressure signal template; further wherein the determining means is configured to determine: that the evoked capture response has been detected if the template matching means determines that the extracted set of pressure data matches the evoked pressure signal template; and that the evoked capture response has not been detected if the template matching means determines that the extracted set of pressure data fails to match the evoked pressure signal template. Such an example is generally shown in FIG. 6A. The extracting means may include operational instructions for execution by the processing module for performing, for example, to obtain the pressure signal as indicated at 604. The template matching means may include operational instructions for execution by the processing module for performing, for example, as shown at 606. The determining means may include operational instructions for execution by the processing module for performing, for example, the determination at 608 and 610/612. In a further extension of this fourth illustrative example, the operational circuitry further comprises initialization means to initialize the feature threshold, wherein the initialization means comprises: therapy means to direct the pacing means to deliver one or more electrical pacing stimuli to the heart of the patient using the at least first and second electrodes and using pacing parameters that are expected to capture the heart; and template means to form an evoked pressure signal template; such an embodiment is shown in FIG. 6B.

In another variant on the fourth illustrative example, the medical device further comprises a posture sensor (such as posture sensor 208), wherein the operational circuitry is configured to store a plurality of template evoked pressure signal templates corresponding to at least first and second postures of the patient.

In some variants of the third and fourth illustrative examples, confirming means may be included. The confirming means may include operational instructions for execution by the processing module for performing, for example, as shown at 562 (FIG. 5B) or 672 (FIG. 6B), obtaining confirmation of capture from a cardiac electrogram as noted at 564/674 (using, for example, the EGM sensor 206 of FIG. 2), or obtaining confirmation from a second device as noted at 566/676 (using, for example, telemetry module 202 of FIG. 2).

In another variant of any of the first to fourth illustrative example, the medical device takes the form of a leadless cardiac pacemaker configured for implantation and operation within a patient's heart.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various to combinations or permutations. The scope of the invention should be determined with reference to the appended claims, along with the full scope of equivalents to which such claims are entitled.

The claimed invention is:

1. An implantable medical device in the form of a cardiac pacemaker, comprising:
    at least first and second electrodes for at least one of delivering therapy or sensing electrical signals;
    a pressure sensor for sensing intracardiac pressure;
    operational circuitry coupled to the electrodes and the pressure sensor; and
    a housing sized and adapted for placement in or on the heart of a patient, the housing containing at least the operational circuitry;
    wherein the operational circuitry is configured to perform a pressure based capture verification process including the following:
    deliver an electrical pacing stimulus to the heart of a patient using the at least first and second electrodes;
    obtaining a pressure signal received with the pressure sensor over a period of time following delivery of the electrical pacing stimulus;
    monitor for an evoked capture response indicating the electrical pacing stimulus was captured using the pressure sensor by identifying a peak in the pressure signal and determining a temporal relationship of the peak in the pressure signal to a second signal event; and
    if the evoked capture response is detected, conclude that the electrical pacing stimulus captured at least a portion of the patient's heart; and
    if the evoked capture response is not detected, conclude that the electrical pacing stimulus did not capture the patient's heart.

2. The medical device of claim 1 wherein the operational circuitry is configured to monitor for an evoked capture response by obtaining a signal received with the pressure sensor over a period of time following delivery of the electrical pacing stimulus, extracting a feature from the pressure signal, and comparing the extracted feature to a feature threshold, such that:
    if the feature threshold is exceeded, the operational circuitry is configured to conclude that the evoked capture response has been detected; and
    if the feature threshold is not exceeded, the operational circuitry is configured to conclude that the evoked capture response has not been detected.

3. The medical device of claim 2 wherein the extracted feature is a peak pressure during systole and the feature threshold is a pressure threshold.

4. The medical device of claim 2 wherein the extracted feature is a minimum pressure during diastole, and the feature threshold is a minimum pressure threshold for diastole.

5. The medical device of claim 2 wherein the extracted feature is a peak rate of change of pressure during systole, and the feature threshold is a minimum rate of change of pressure.

6. The medical device of claim 2 wherein the extracted feature is a minimum rate of change of pressure, and the feature threshold is a minimum rate of change of pressure.

7. The medical device of claim 2 wherein the extracted feature is an area under the curve of a measured pressure over a period of time, and the feature threshold is a minimum area.

8. The medical device of claim 2 wherein the operational circuitry is configured to perform an evoked pressure signal initialization process in which:
    the operational circuitry issues one or more electrical pacing stimulus to the heart of the patient using the at least first and second electrodes, the one or more electrical pacing stimulus being delivered using pacing parameters that are expected to capture the heart;

the operational circuitry obtains signals from the pressure sensor and determines an expected feature value using obtained pressure signals corresponding to evoked capture responses;

the operational circuitry sets the feature threshold in relation to the expected feature value.

9. The medical device of claim 2 wherein the operational circuitry is configured to perform an evoked pressure signal initialization process in which:

the medical device communicates with a second device, the second device being configured to determine whether pacing pulses delivered by the medical device capture the heart;

the operational circuitry issues at least one electrical pacing stimulus to the heart of the patient using the at least first and second electrodes and receives confirmation from the second device that capture has occurred generating one or more confirmed evoked capture responses;

the operational circuitry obtains signals from the pressure sensor and determines an expected feature value corresponding to the one or more confirmed evoked capture responses;

the operational circuitry sets the feature threshold in relation to the expected feature value.

10. The medical device of claim 2 wherein the operational circuitry is configured to perform an evoked pressure signal initialization process in which:

the operational circuitry issues at least one electrical pacing stimulus to the heart of the patient using the at least first and second electrodes;

the operational circuitry analyzes an electrical signal sensed from the heart and determines that capture has occurred generating one or more confirmed evoked capture responses;

the operational circuitry obtains signals from the pressure sensor and determines an expected feature value corresponding to the one or more confirmed evoked capture responses;

the operational circuitry sets the feature threshold in relation to the expected feature value.

11. The medical device of claim 1 wherein the operational circuitry is configured to monitor for an evoked capture response by obtaining a signal received with the pressure sensor over a period of time following delivery of the electrical pacing stimulus, and comparing the obtained pressure signal to an evoked pressure signal template, such that:

if the evoked pressure signal template matches the obtained pressure signal, the operational circuitry is configured to conclude that the evoked capture response has been detected; and if the evoked pressure signal template fails to match the obtained pressure signal, the operational circuitry is configured to conclude that the evoked capture response has not been detected.

12. The medical device of claim 11 wherein the operational circuitry is configured to perform an evoked pressure signal initialization process in which:

the operational circuitry issues one or more electrical pacing stimulus to the heart of the patient using the at least first and second electrodes, the one or more electrical pacing stimulus being delivered at an energy that is expected to capture the heart;

the operational circuitry obtains signals from the pressure sensor and determines an evoked pressure signal template.

13. The medical device of claim 11 wherein the operational circuitry is configured to perform an evoked pressure signal initialization process in which:

the medical device communicates with a second device, the second device being configured to determine whether pacing pulses delivered by the medical device capture the heart;

the operational circuitry issues at least one electrical pacing stimulus to the heart of the patient using the at least first and second electrodes and receives confirmation from the second device that capture has occurred generating one or more confirmed evoked capture responses;

the operational circuitry obtains signals from the pressure sensor corresponding to the confirmed evoked capture responses, and determines an evoked pressure signal template.

14. The medical device of claim 11 wherein the operational circuitry is configured to perform an evoked pressure signal initialization process in which:

the operational circuitry issues at least one electrical pacing stimulus to the heart of the patient using the at least first and second electrodes;

the operational circuitry analyzes an electrical signal sensed from the heart and determines that capture has occurred generating one or more confirmed evoked capture responses;

the operational circuitry obtains signals from the pressure sensor corresponding to the confirmed evoked capture responses, and determines an evoked pressure signal template.

15. The medical device of claim 11 further comprising a posture sensor, wherein the operational circuitry is configured to store a plurality of evoked pressure signal templates corresponding to at least first and second postures of the patient.

16. The medical device of claim 1 wherein the operational circuitry is configured to determine a temporal relationship of the peak in the pressure signal to the second signal event by:

identifying a first point in time at which the peak in the pressure signal occurs;

identifying a second point in time at which a selected cardiac event takes place using a heart sound, the heart sound being the second signal event, the heart sound relating to an atrial event, wherein the electrical pacing stimulus is configured to excite a ventricle;

calculating an interval between the first and second points in time; and determining whether an evoked capture response has been detected using the interval; wherein:

if the interval is shorter than a threshold, the operational circuitry is configured to conclude that the evoked capture response has occurred; and if the interval is longer than a threshold, the operational circuitry is configured to conclude that the evoked capture response has not occurred.

17. The medical device of claim 1 wherein the operational circuitry is configured to determine a temporal relationship of the peak in the pressure signal to the second signal event by;

determining an R-wave time at which the electrical R-wave signal of the heart occurs following the electrical pacing stimulus, the R-wave time being the second signal event;

determining a pressure time at which the peak in the pressure signal occurs;

calculating an interval between the R-wave time and the pressure time;

comparing the interval to a threshold and:

if the interval exceeds the threshold, determining that the evoked capture response has occurred; and if the interval does not exceed the threshold, determining that the evoked capture response has not occurred.

18. The medical device of claim 1 further comprising a motion sensor, wherein the operational circuitry is configured to determine a temporal relationship of the peak in the pressure signal to the second signal event;

determining a motion time at which the motion sensor detects cardiac movement following the electrical pacing stimulus, the motion time being the second signal event;

determining a pressure time at which the peak in the pressure signal occurs;

determining whether each of:

a) the pressure signal exceeds a pressure threshold; and b) the motion time and the pressure time temporally correlate to one another;

if both a) and b) occur, determining that the evoked capture response has occurred; and if one or both of a) and b) do not occur, determining that the evoked capture response has not occurred.

19. An implantable medical device in the form of a cardiac pacemaker, comprising:

at least first and second electrodes for at least one of delivering therapy or sensing electrical signals;

a pressure sensor for sensing intracardiac pressure;

operational circuitry coupled to the electrodes and the pressure sensor; and a housing sized and adapted for placement in or on the heart of a patient, the housing containing at least the operational circuitry;

wherein the operational circuitry is configured to obtain a pressure signal received with the pressure sensor over a period of time following delivery of the electrical signals;

wherein the operational circuitry is configured to perform a pressure based capture verification process by using the pressure sensor to determine whether a delivered pacing therapy to the heart of a patient has generated an evoked response by identifying a peak in the pressure signal and determining a temporal relationship of the peak in the pressure signal to a second signal event; and wherein the operational circuitry is configured to perform an electrical pacing capture verification process by using an electrical signal captured via the at least first and second electrodes to determine whether a delivered pacing therapy to the heart of a patient has generated an evoked response;

wherein the operational circuitry is configured to use one, the other, or both of the pressure based capture verification process and the electrical pacing capture verification process to assess efficacy of pacing stimuli.

20. A method of verifying pacing capture in an implantable cardiac pacemaker comprising at least first and second electrodes for at least one of delivering therapy or sensing electrical signals, a pressure sensor for sensing intracardiac pressure, operational circuitry coupled to the electrodes and the pressure sensor configured to obtain a pressure signal received with the pressure sensor over a period of time following delivery of the electrical signals, and a housing sized and adapted for placement in or on the heart of a patient, the housing containing at least the operational circuitry;

wherein the method comprises:

delivering an electrical pacing stimulus to the heart of a patient using the at least first and second electrodes;

monitoring for an evoked capture response indicating the electrical pacing stimulus was captured using the pressure sensor by identifying a peak in the pressure signal and determining a temporal relationship of the peak in the pressure signal to a second signal event; and if the evoked capture response is detected, concluding that the electrical pacing stimulus captured at least a portion of the patient's heart; and if the evoked capture response is not detected, concluding that the electrical pacing stimulus did not capture the patient's heart.

* * * * *